(12) United States Patent
Warner et al.

(10) Patent No.: US 8,118,880 B1
(45) Date of Patent: Feb. 21, 2012

(54) COLORING COMPOSITION CONTAINING L-DOPA AND L-ARGININE AND FORMING A NON-COVALENT DERIVATIZATION COMPLEX

(75) Inventors: John C. Warner, Wilmington, MA (US); Emily J. Stoler, Wilmington, MA (US)

(73) Assignees: Warner Babcock Institute for Green Chemistry, LLC, Wilmington, MA (US); John Masters Organic Hair Care, Inc., New York, NY (US)

( * ) Notice: Subject to any disclaimer, the term of this patent is extended or adjusted under 35 U.S.C. 154(b) by 0 days.

(21) Appl. No.: 12/946,461

(22) Filed: Nov. 15, 2010

(51) Int. Cl.
  *C09B 67/00* (2006.01)
(52) U.S. Cl. ............. 8/401; 8/405; 8/406; 8/552; 8/563; 8/584; 8/594; 8/616
(58) Field of Classification Search .............. 8/401, 405, 8/406, 552, 563, 584, 594, 616
  See application file for complete search history.

(56) References Cited

U.S. PATENT DOCUMENTS

| 4,021,538 A | 5/1977 | Yu et al. | |
|---|---|---|---|
| 2004/0040097 A1* | 3/2004 | Dreher et al. | 8/405 |
| 2004/0261198 A1 | 12/2004 | Kainz et al. | |
| 2005/0175556 A1 | 8/2005 | Gupta | |
| 2008/0292545 A1 | 11/2008 | Lin et al. | |
| 2009/0178209 A1 | 7/2009 | Koike et al. | |

FOREIGN PATENT DOCUMENTS

| EP | 1676582 | 7/2006 |
|---|---|---|
| WO | WO8909833 | 10/1989 |

OTHER PUBLICATIONS

John C. Warner, Entropic Control in Green Chemistry and Materials Design, Pure Appl. Chem., vol. 78, No. 11, pp. 2035-2041, 2006.
John C. Warner, Final Report: Pollution Prevention With the Use of Molecular Assemblies, National Center for Environmental Research, http://cfpub.epa.gov/ncer_abstracts/index.cfm/fuseaction/display.abstractDetail/abstract/126/report/0, EPA Grant No. R825327, as of Aug. 31, 2010.
John C. Warner, About Non-Covalent Derivatization, Warner Babcock Institute For Green Chemistry: Partner With WBI, http://www.warnerbabcock.com/partner_with_wbi/non-covalent_derivatization.asp, as of Aug. 31, 2010.

* cited by examiner

*Primary Examiner* — Eisa Elhilo
(74) *Attorney, Agent, or Firm* — George R. McGuire; Blaine T. Bettinger; Bond Schoeneck & King

(57) ABSTRACT

A natural coloring composition for coloring materials, and methods of its use. The coloring composition comprises a natural precursor aromatic ring molecule such as L-DOPA that is oxidatively oligomerized or polymerized in the presence of arginine and an activator, such as a salt or an enzyme, wherein the L-DOPA and the amino acid form a specific non-covalent interaction. The natural coloring composition can also include a buffer, colorant, stabilizer, and/or thickening agent, and can comprise one or two inactive solutions that are combined to form an active coloring composition.

22 Claims, 28 Drawing Sheets

L-DOPA

L-DOPA

100% L-DOPA, 0% ARGININE

75% L-DOPA, 25% ARGININE

COLORING COMPOSITION CONTAINING L-DOPA AND L-ARGININE AND FORMING A NON-COVALENT DERIVATIZATION COMPLEX

CROSS-REFERENCE TO RELATED APPLICATIONS

The present application is related to U.S. Provisional Patent Application No. 61/261,287, filed on Nov. 13, 2009 and entitled "The Use of Tyrosinase Enzymatic Oxidation For Hair Coloring," and U.S. Provisional Patent Application No. 61/261,290, filed on Nov. 13, 2009 and entitled "The Use of L-DOPA Oxidation For Hair Coloring," the content of each of which is relied upon and incorporated herein by reference in its entirety.

BACKGROUND OF THE INVENTION

1. Field of the Invention

The present invention relates to a coloring composition and methods of its use, and, more specifically, to a non-covalent derivatization coloring composition containing L-DOPA and arginine.

2. Description of the Related Art

Materials have been dyed and colored for thousands of years. While natural substances have historically been used to color most materials, these substances are often unable to permanently dye many types of materials. There is, therefore, a large demand for synthetic dye formulations that permanently color a material, including natural and artificial fibers, among many other beneficial uses. One of the largest markets for permanent dye formulations is the hair coloring market.

Most permanent hair color products contain a developer and an alkalizing agent. The developer is usually an oxidizing agent such as hydrogen peroxide in a water or a cream lotion, and the alkalizing agent is most often ammonia or an ammonia substitute. These chemicals cause the hair to swell and thus allow the pigment to penetrate the hair cuticle deep enough to reach and replace the natural melanin.

Several studies have suggested that the chemicals found in synthetic hair dyes, including ammonia, lead, and/or coal tar, are toxic and can have dangerous side-effects such as hair loss, burning, redness, itchy skin, swelling, or trouble breathing. As a result, many people decide to forego hair dyes to avoid exposure to the chemicals found in the coloring compositions. Although there are some natural formulations that employ compounds found in nature, they tend to be inconsistent and most often temporary.

As a result, there is a continued need for coloring compositions that use natural compounds rather than synthetic chemicals to permanently color material such as hair. Additionally, there is a continued demand for efficient and environmentally-friendly formulations and methods for coloring materials either permanently or semi-permanently.

One possible component of natural coloring compositions are natural and/or organic molecules that form non-covalent interactions with color polymers. While traditional methods of synthesis use synthetic chemicals such as solvents to form chemical products, non-covalent derivitization ("NCD") uses the natural non-covalent intermolecular interactions between a directing material and a target compound to modify the properties of the target compound. When the directing material and the target compound interact, the resulting derivative possesses properties that can be significantly different from either the target compound or the directing material alone. Often, the properties of the derivative can be modified by altering the ratio of target compound to directing material, and/or changing the directing material. Another benefit of the NCD method is that the directing material and the target compound are typically both incorporated into the product, thereby eliminating at least some waste during production.

Thus, there is a continued need for organic coloring compositions that permanently or semi-permanently color compounds. Additionally, there is a continued need for a wide variety of coloring compositions to satisfy many different coloring needs.

BRIEF SUMMARY OF THE INVENTION

It is therefore a principal object and advantage of the present invention to provide natural precursor aromatic ring molecules that form colored conjugated polymers upon oxidation.

It is another object and advantage of the present invention to provide an organic coloring composition.

It is yet another object and advantage of the present invention to provide an organic coloring composition containing L-DOPA and the enzyme tyrosinase.

It is another object and advantage of the present invention to provide an organic coloring composition containing L-DOPA and an initiator, wherein the initiator is an enzyme.

It is a further object and advantage of the present invention to provide a composition that comprises two or more solutions or suspensions which, when combined, form an organic coloring composition.

It is yet another object and advantage of the present invention to provide a method for coloring a material using an organic coloring composition.

It is another object and advantage of the present invention to provide a method for coloring a material using an organic coloring composition wherein the addition of molecules that form noncovalent interactions with the oligomer or polymer affects the properties of the coloring composition.

It is a further object and advantage of the present invention to provide an organic coloring composition containing molecules that form noncovalent interactions with the oligomer or polymer.

It is yet another object and advantage of the present invention to provide an organic coloring composition containing molecules that form noncovalent interactions with the oligomer or polymer and stabilize oxidation, precipitation, and/or agglomeration.

Other objects and advantages of the present invention will in part be obvious, and in part appear hereinafter.

In accordance with the foregoing objects and advantages, the present invention provides a coloring composition comprising: (i) L-DOPA; (ii) an initiator; and (iii) L-arginine, where the L-DOPA is oxidized in the presence of the initiator to form a color polymer, and the L-DOPA forms a non-covalent interaction with the L-arginine. In one embodiment, the initiator is a salt or a protein. The salt can be any salt known in the art, including without limitation potassium hexacyanoferrate, potassium bicarbonate, and combinations thereof. The protein can be an enzyme including, without limitation, horseradish peroxidase and/or tyrosinase, among many others known in the art.

A second aspect of the present invention provides the following coloring composition comprising: (i) L-DOPA; (ii) an initiator; and (iii) L-arginine, where the L-DOPA is oxidized in the presence of the initiator to form a color polymer, and the L-DOPA forms a non-covalent interaction with the L-arginine. In this embodiment, the aromatic compound is part of a first solution, and the initiator and amino acid are part of a second solution. These solutions can then be combined by the user at the time of, or just prior to, use.

A third aspect of the present invention provides a coloring composition comprising: (i) L-DOPA; (ii) an initiator; (iii) an amino acid; and (iv) L-arginine, where the L-DOPA is oxidized in the presence of the initiator to form a color polymer, and the L-DOPA forms a non-covalent interaction with the L-arginine. The amino acid can be, for example, B-DEPTA, L-cysteine, L-alanine, L-argenine, or any combination of two or more of these amino acids.

A fourth aspect of the present invention provides a coloring composition comprising: (i) L-DOPA; (ii) an initiator; (iii) a colorant; and (iv) L-arginine, where the L-DOPA is oxidized in the presence of the initiator to form a color polymer, and the L-DOPA forms a non-covalent interaction with the L-arginine. The colorant is preferably an organic compound and can include curcumin, lawsone, emodin, jugalone, plumbagin, L-cysteine, methionine, cystine, glutamine, and combinations thereof, among many other natural and/or organic compounds.

A fifth aspect of the present invention provides a coloring composition comprising: (i) L-DOPA; (ii) an initiator; (iii) L-arginine, where the L-DOPA is oxidized in the presence of the initiator to form a color polymer, and the L-DOPA forms a non-covalent interaction with the L-arginine; and (iv) one or more of the following additives: (a) a buffer (such as a phosphate buffer); (b) a thickening agent; and/or (c) a stabilizer.

A sixth aspect of the present invention provides a method for dyeing a material. The method comprises the step of contacting the material with any of the coloring compositions described herein. The method can further comprise one or more of the following steps: (i) leaving the coloring composition in contact with the material for 1 to 60 minutes; (ii) pre-treating the material with a first pre-treatment solution; (iii) rinsing said material; (iv) drying said material; and/or (v) combining the aromatic compound and the initiator at the time of use.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 4A:
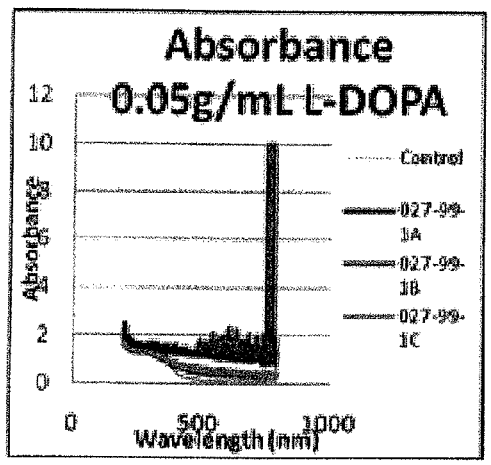
Figure 4B:
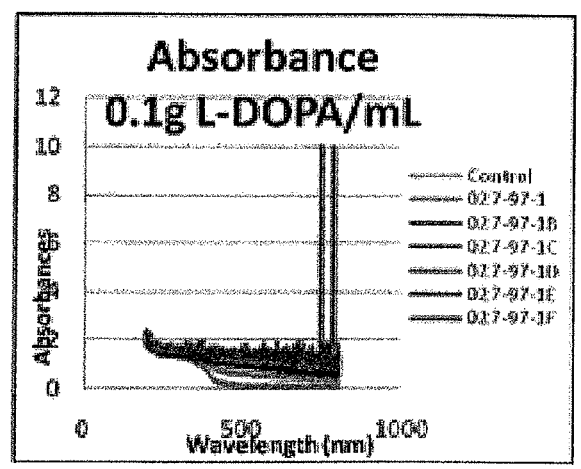
Figure 4C:
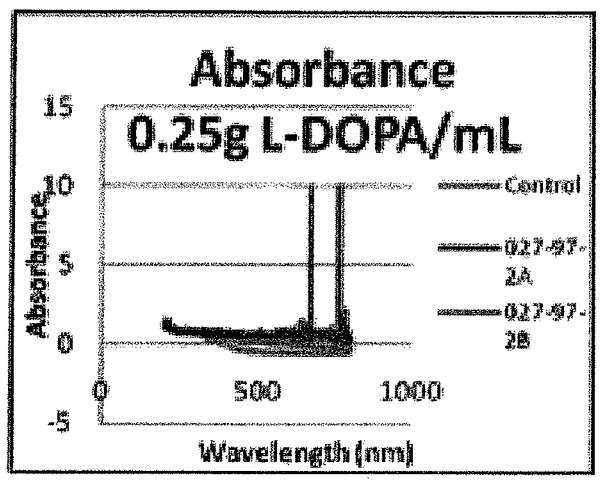
Figure 5A:
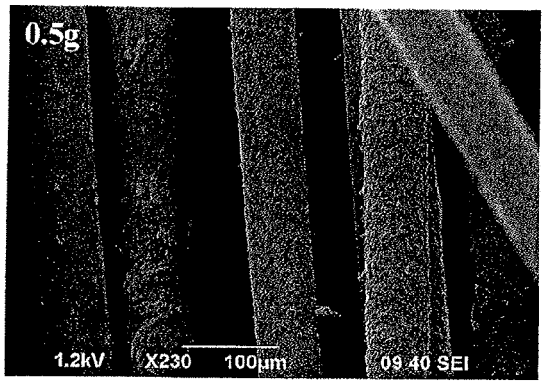
Figure 5B:
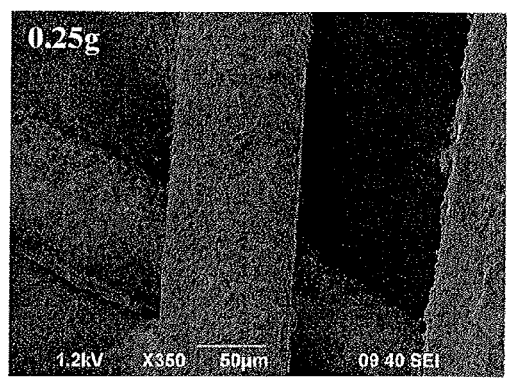
Figure 5C:
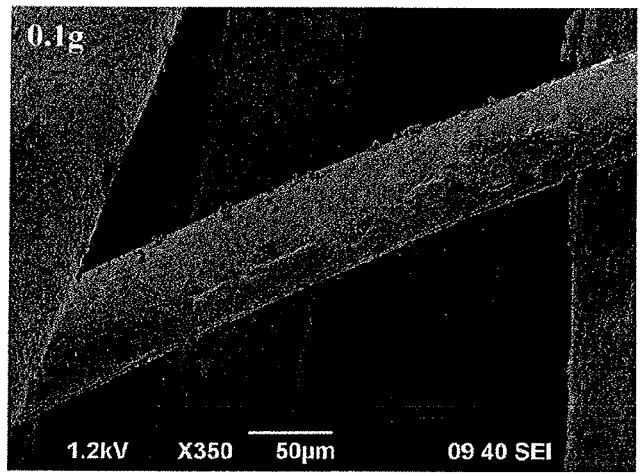
Figure 6A:
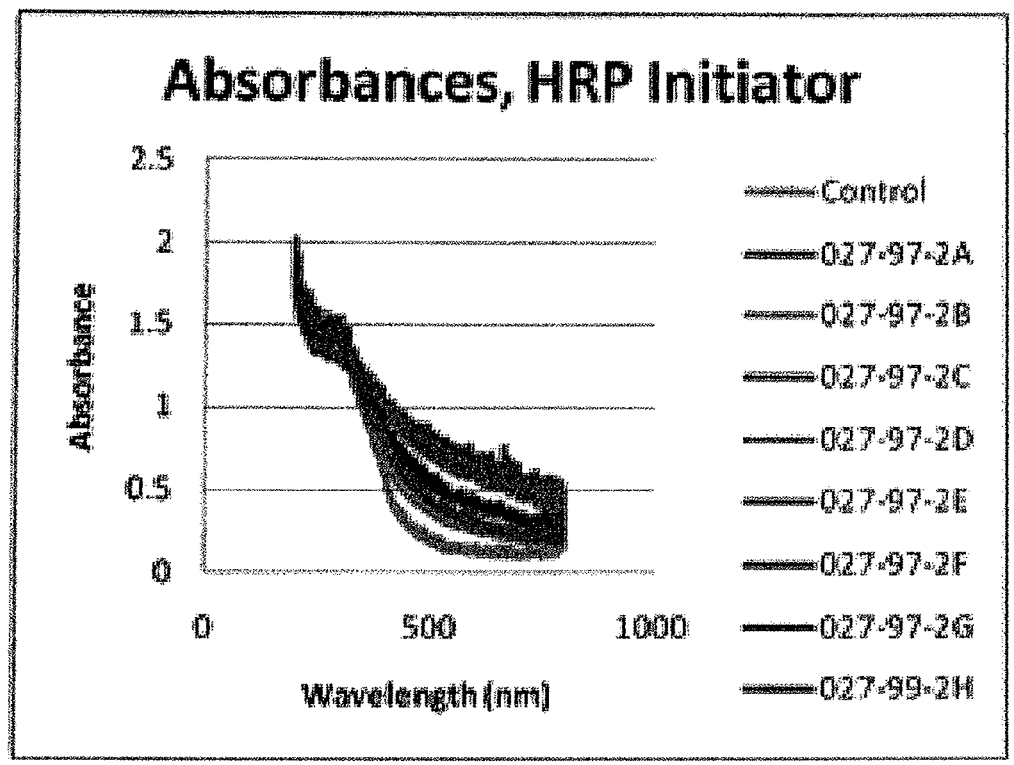
Figure 6B:
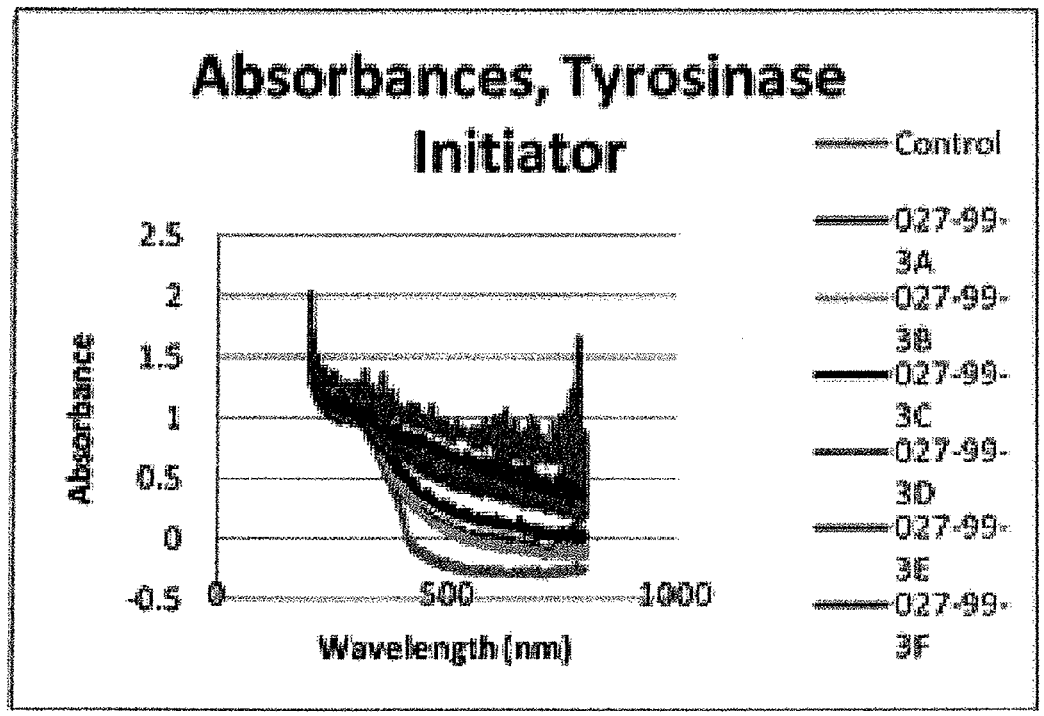
Figure 7A:
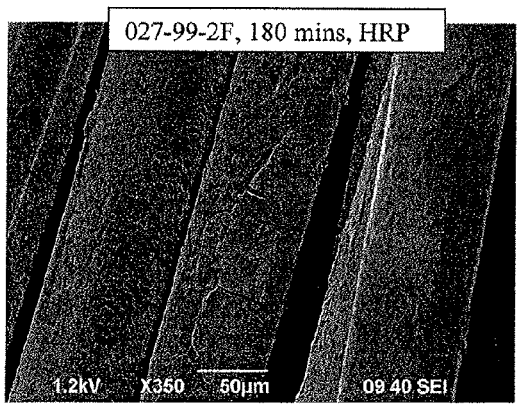
Figure 7B:
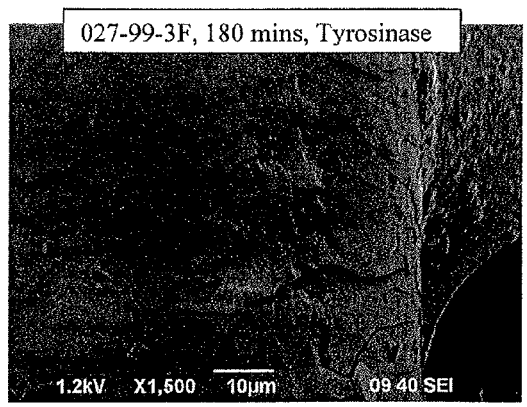
Figure 7C:
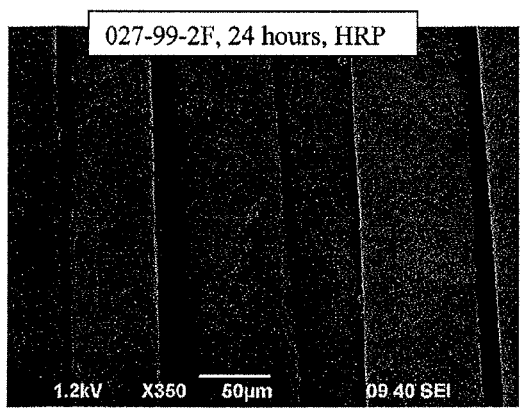
Figure 7D:
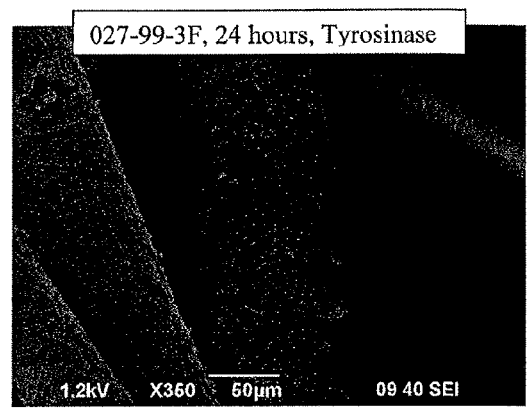
Figure 8:
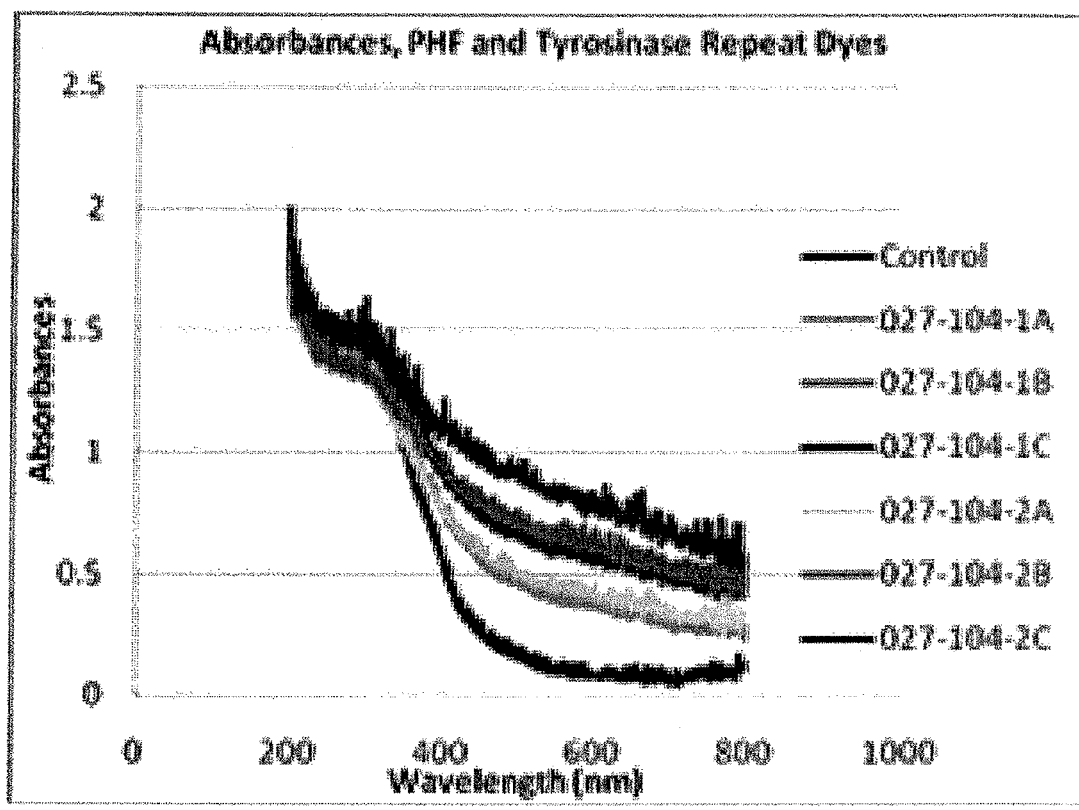
Figure 9:
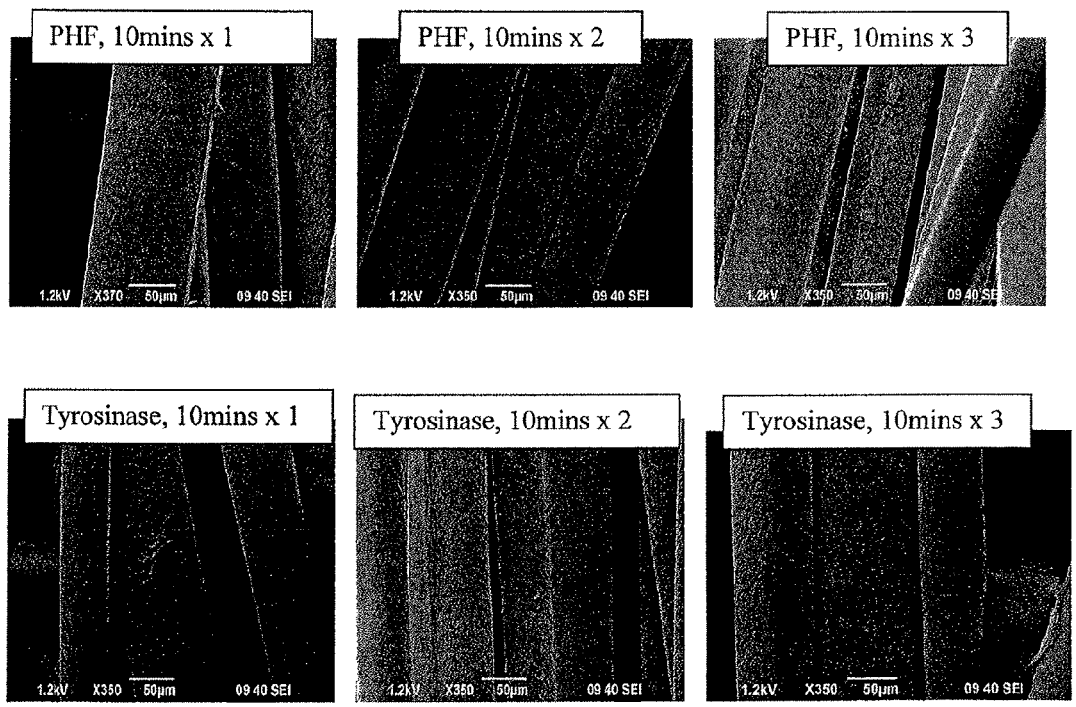
Figure 10:
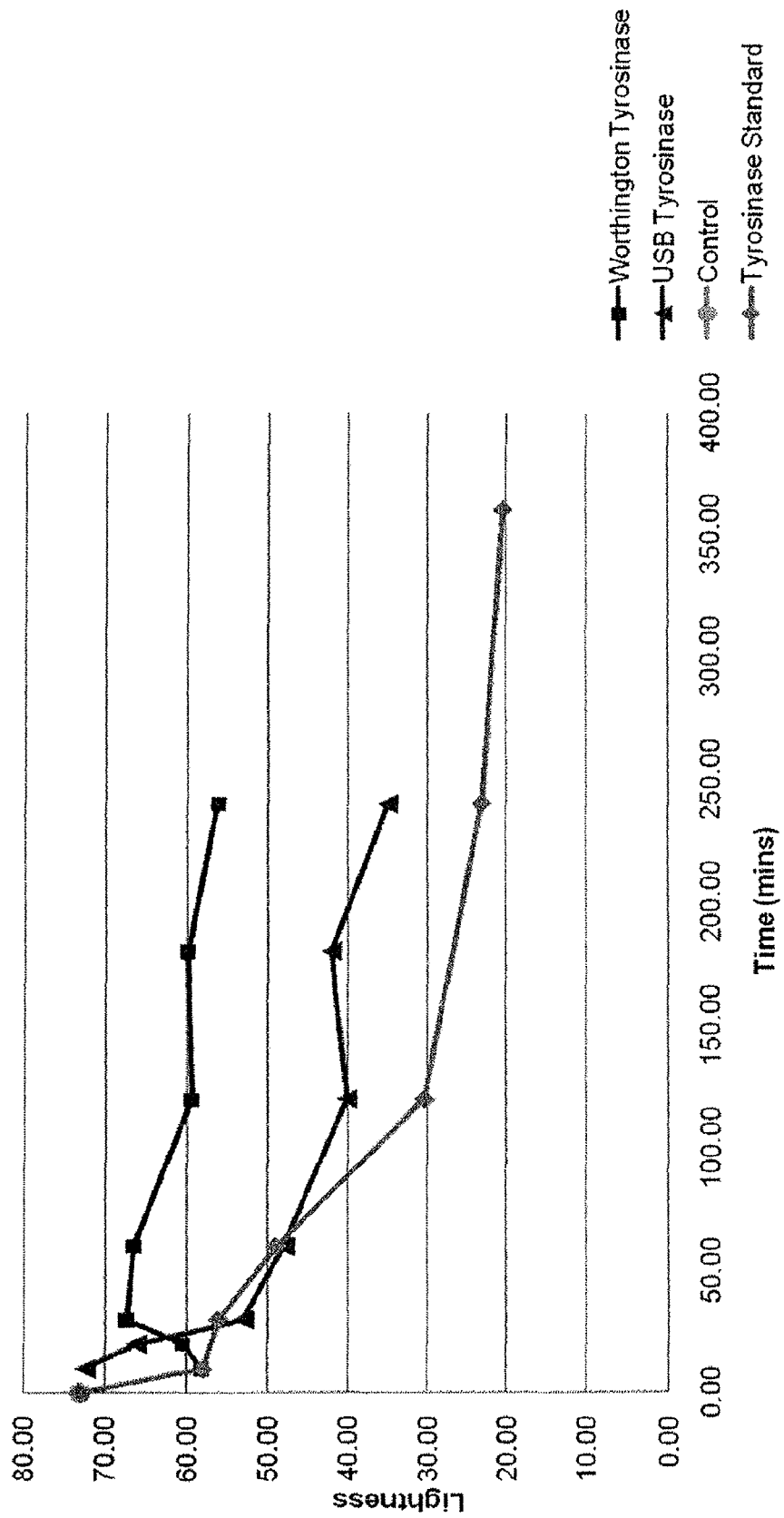
Figure 11:
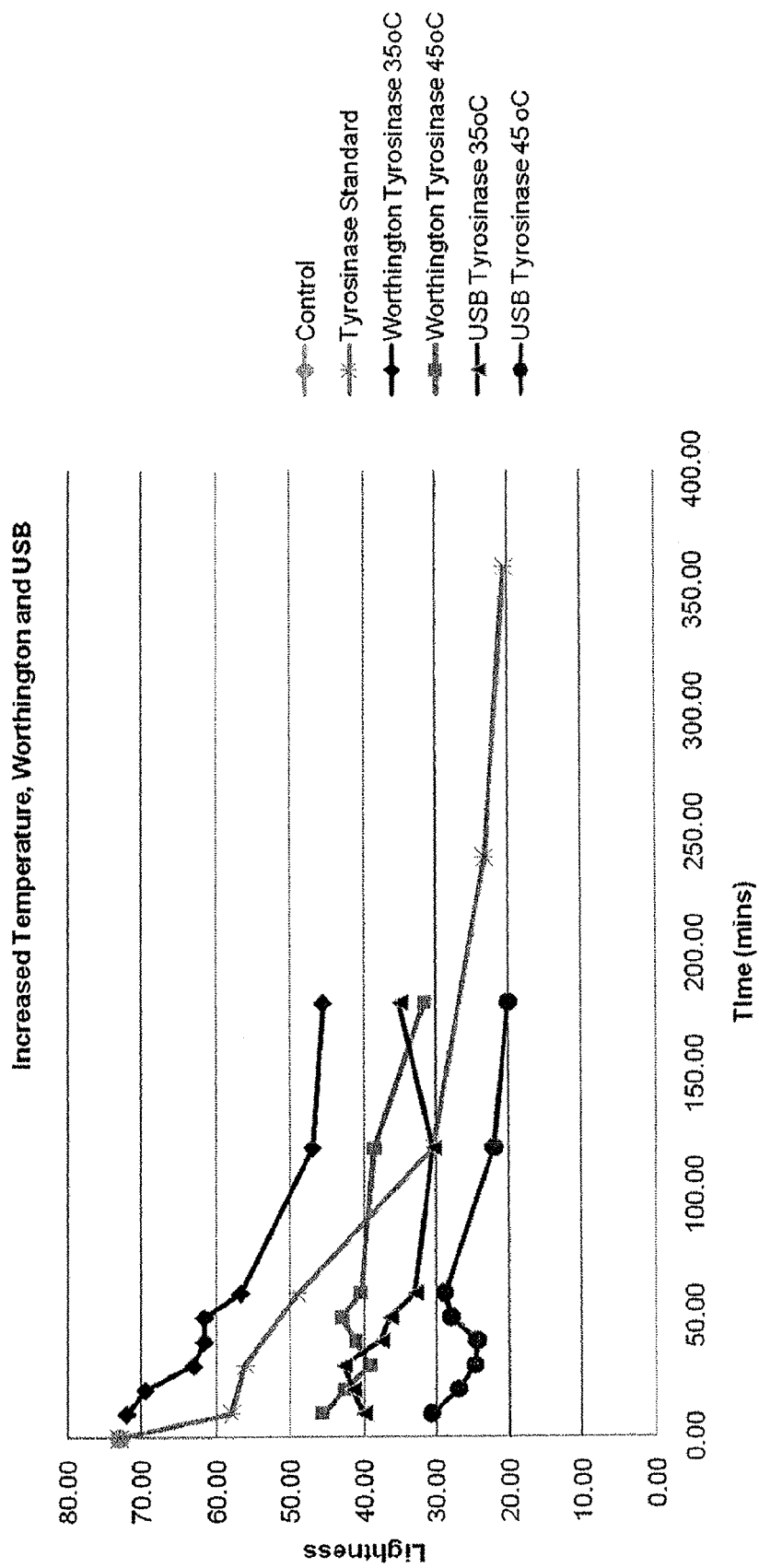
Figure 12:
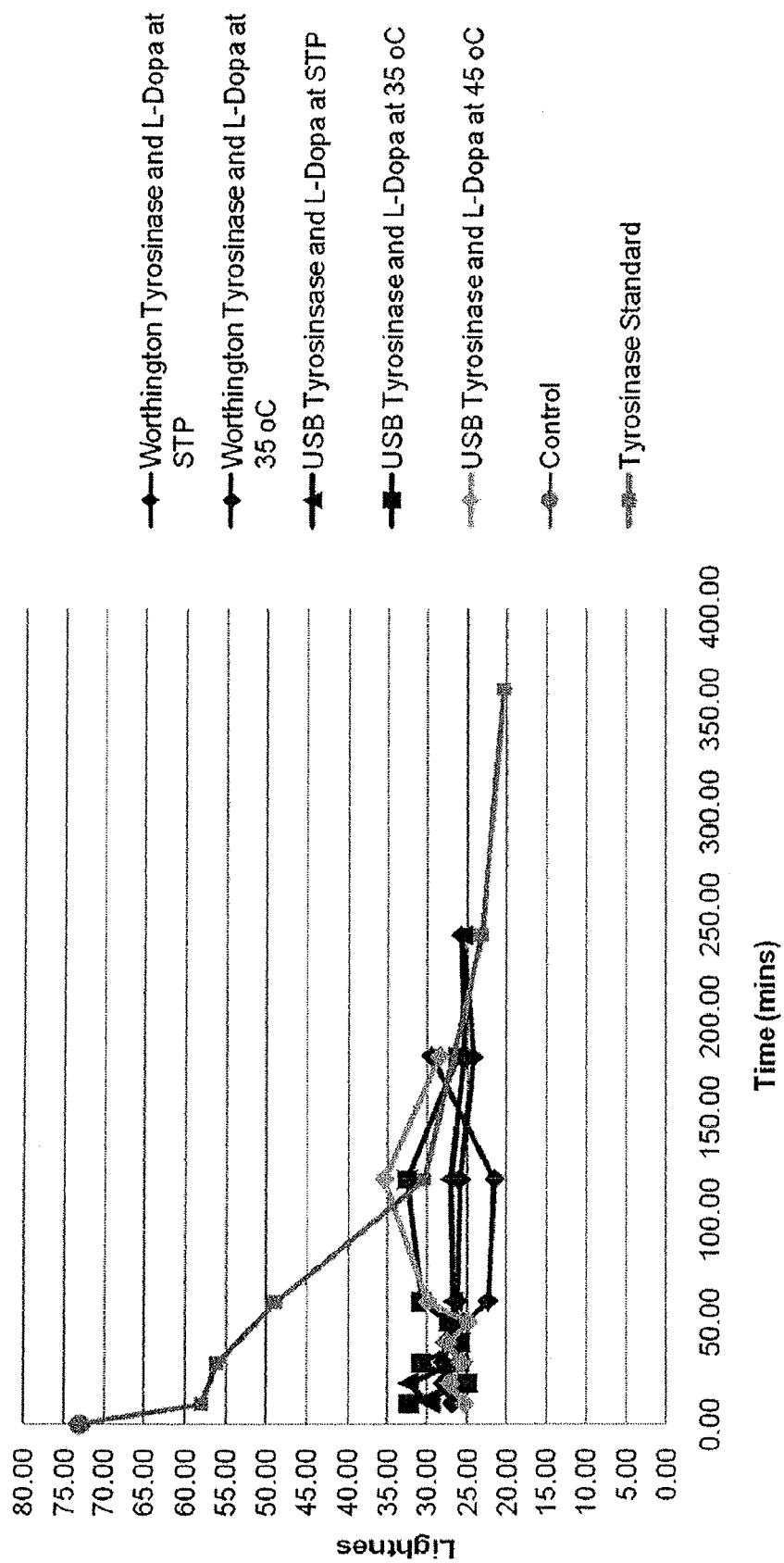
Figure 13:
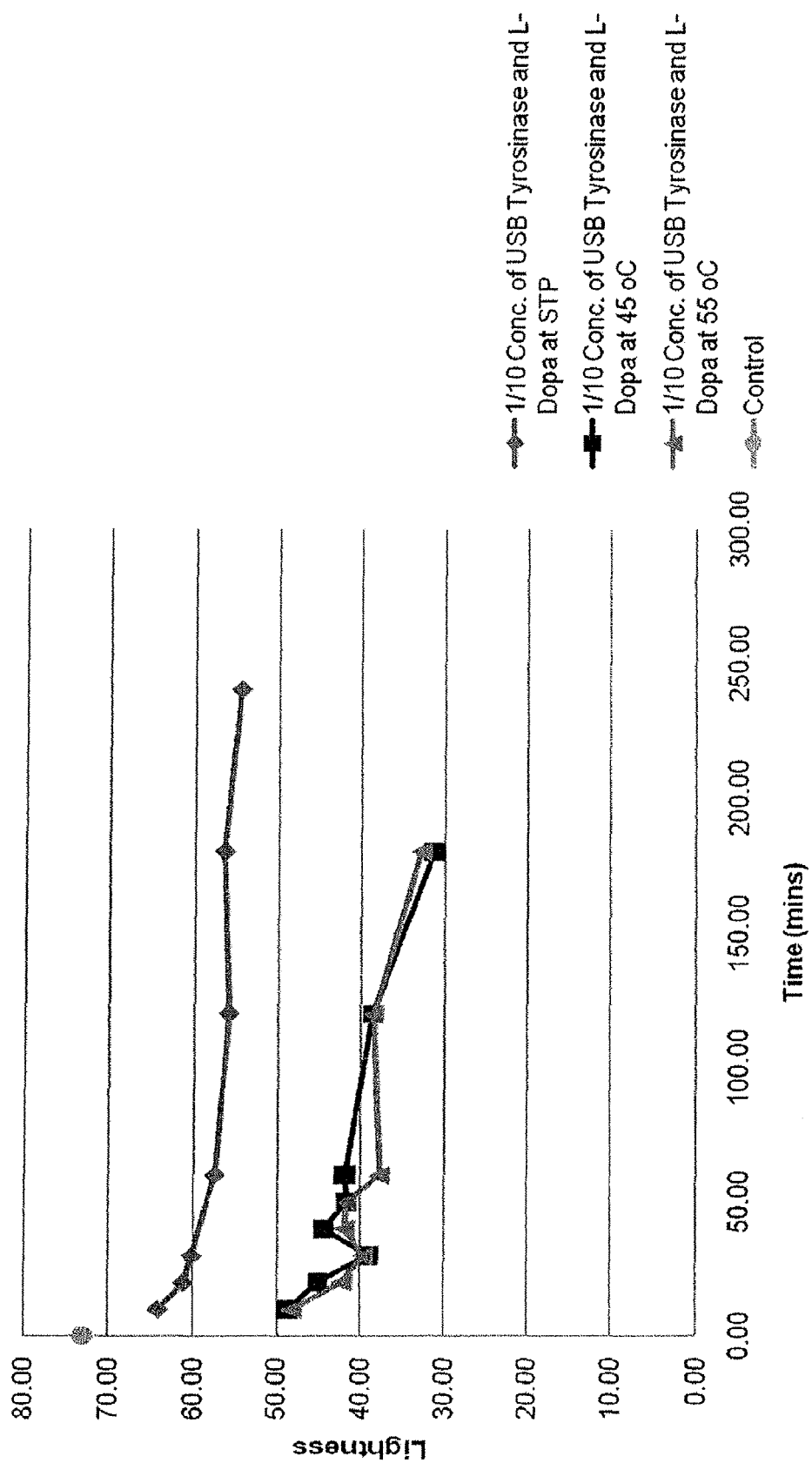
Figure 14:
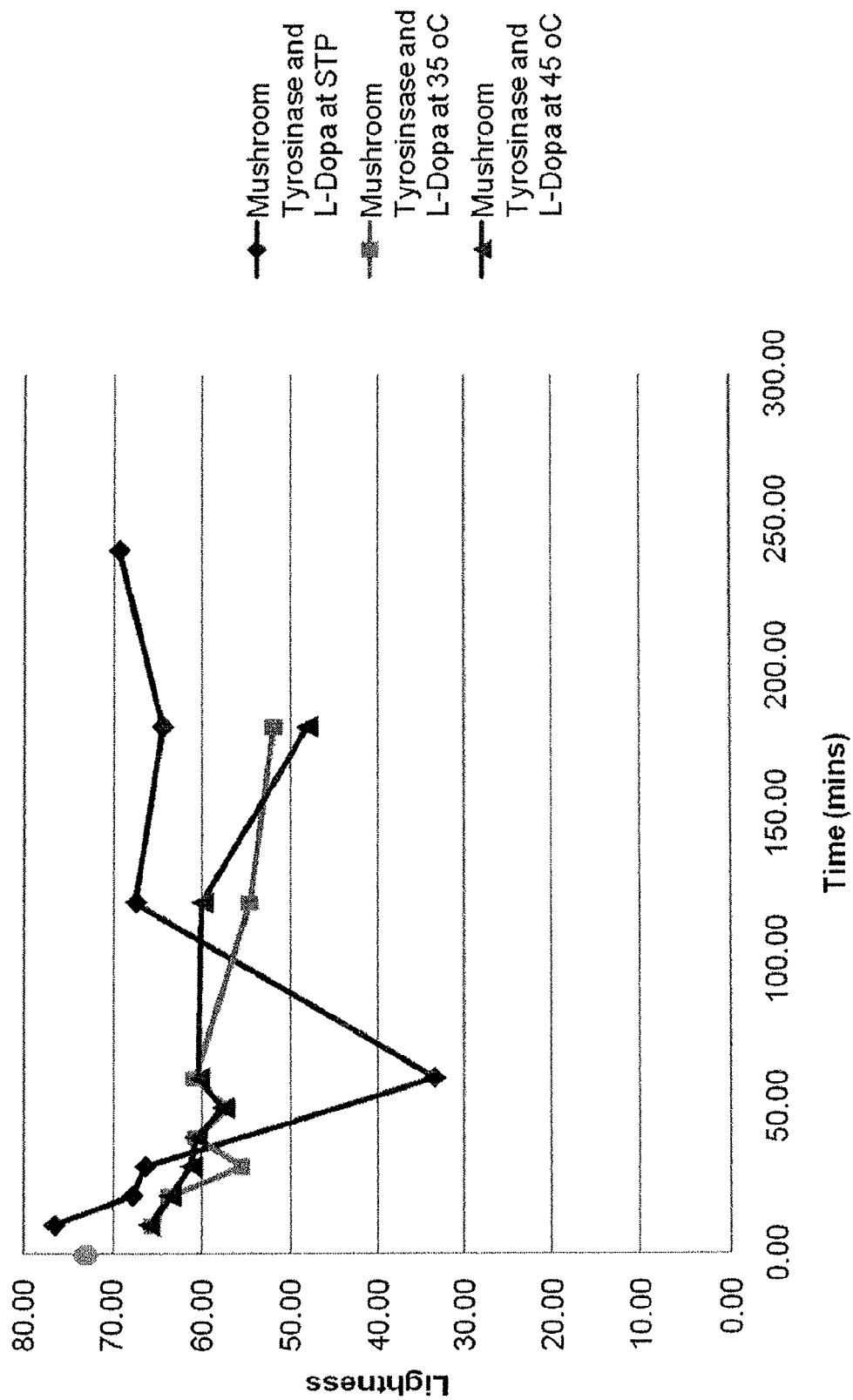
Figure 15:
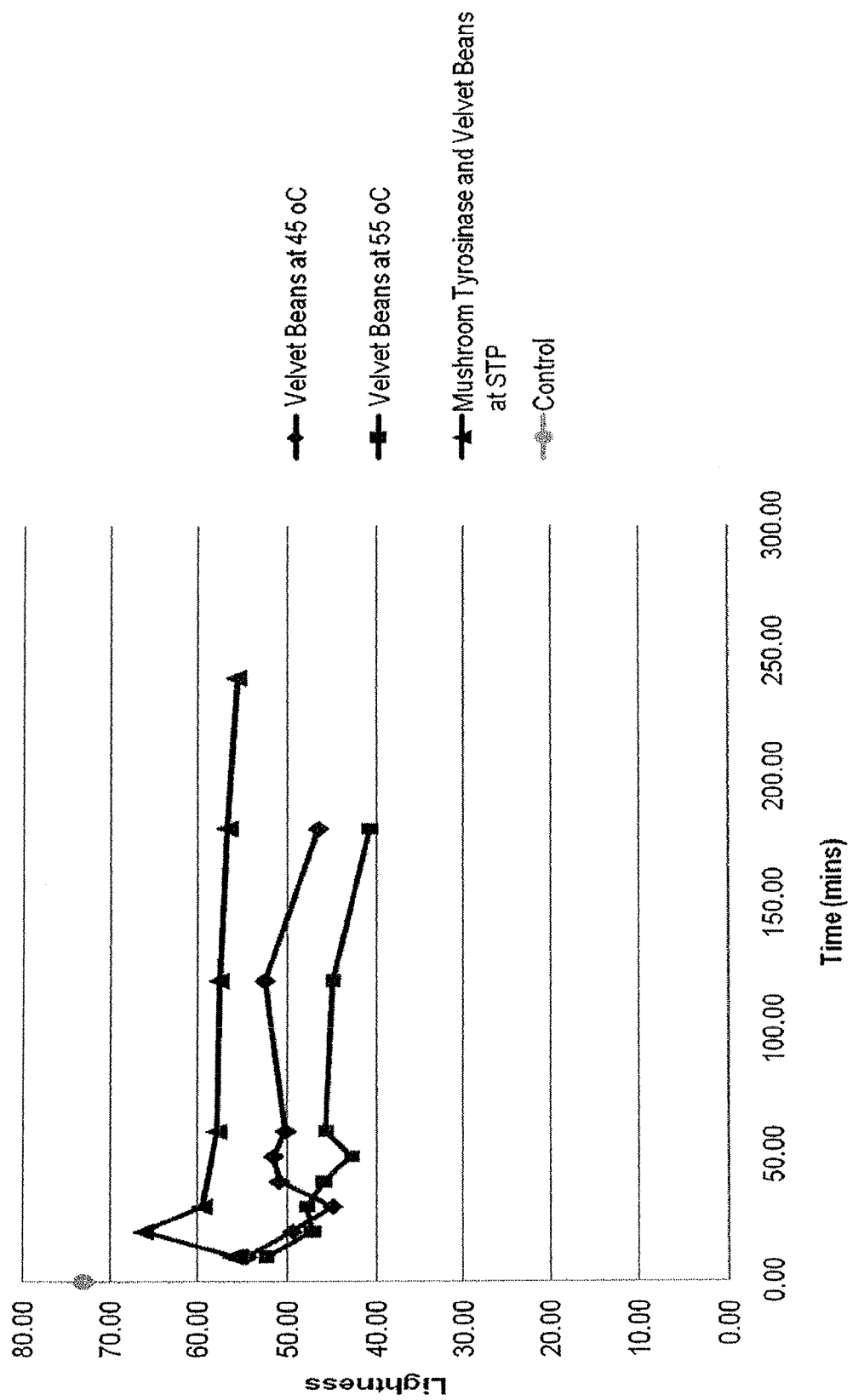
Figure 16:
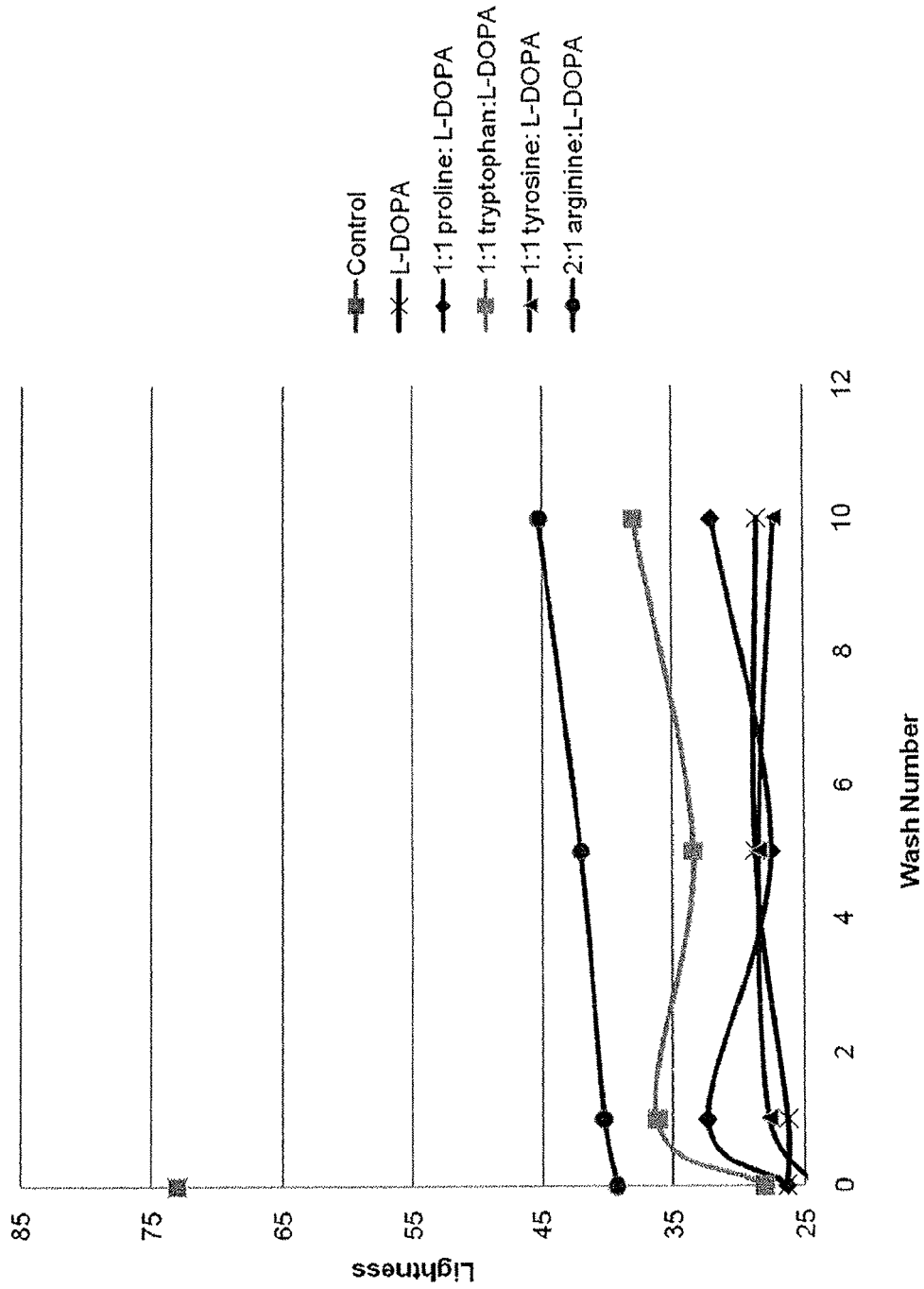
Figure 17:
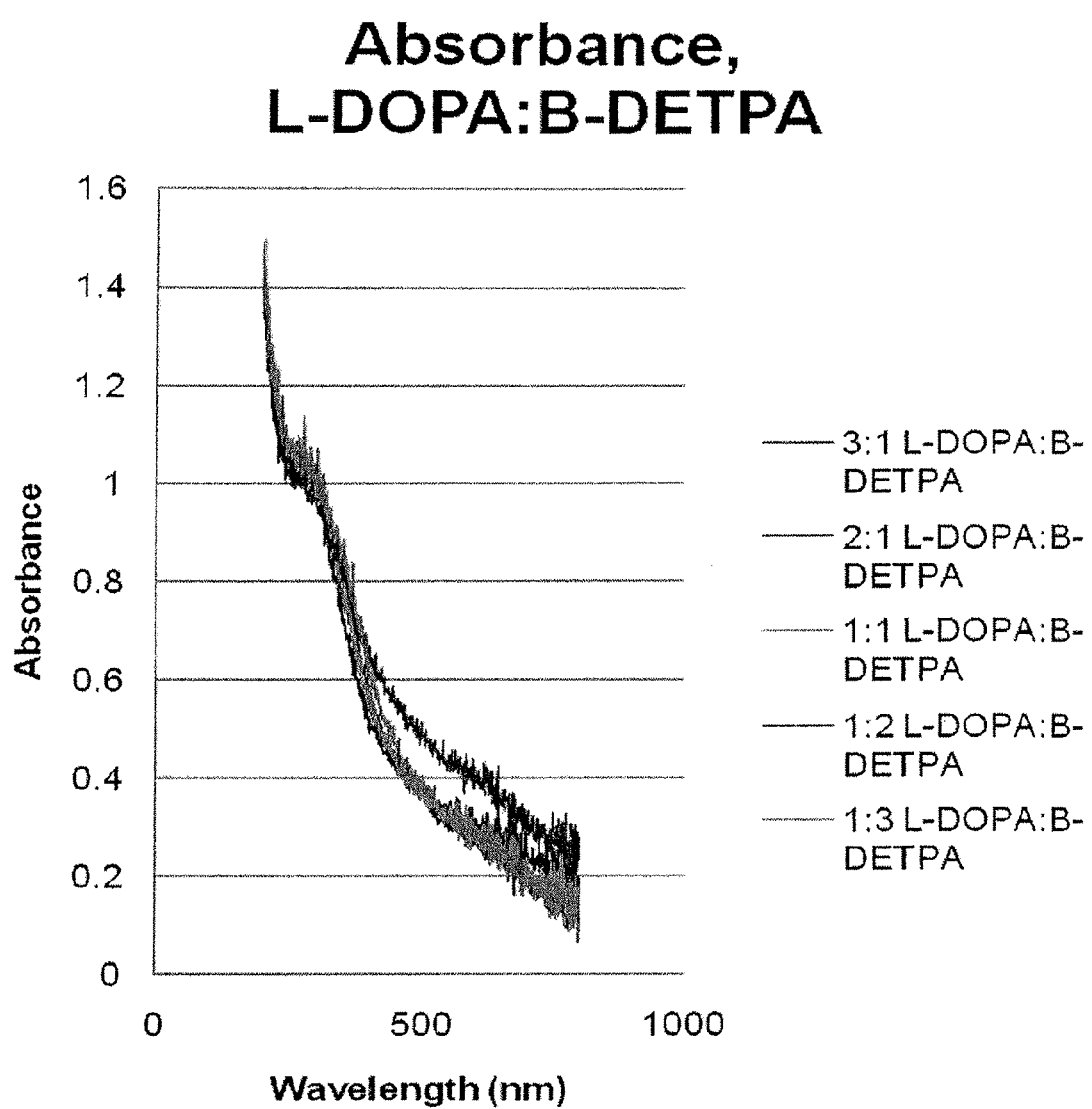
Figure 18:
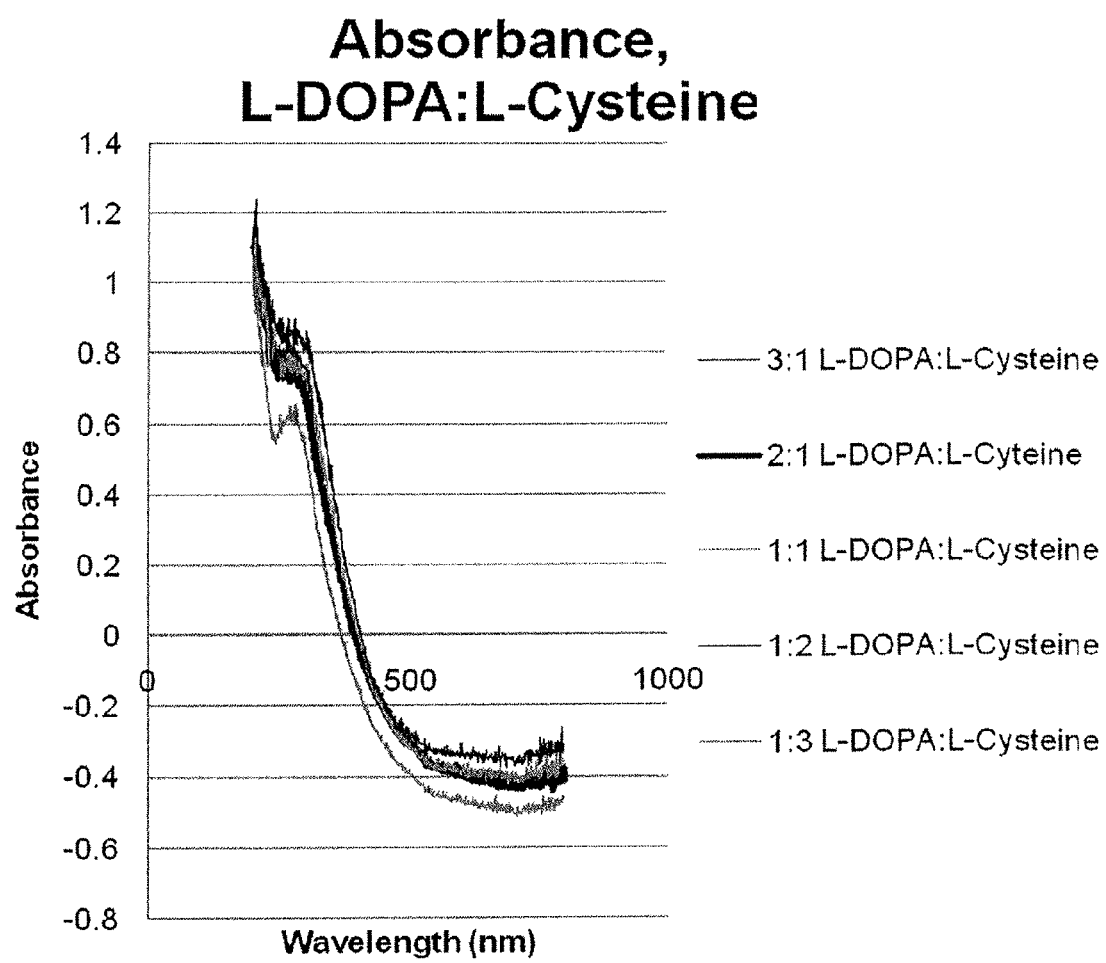
Figure 19:
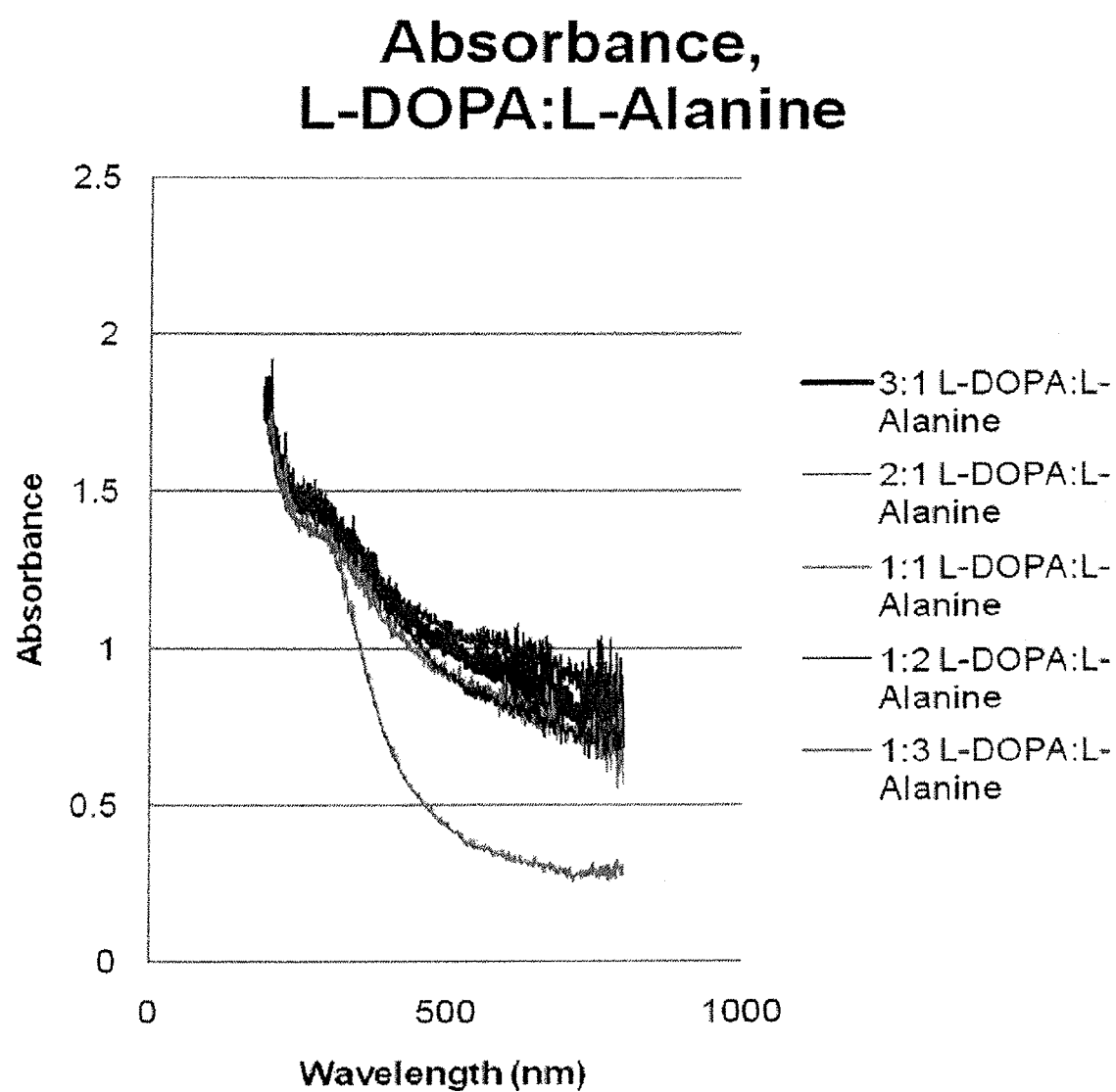
Figure 20:
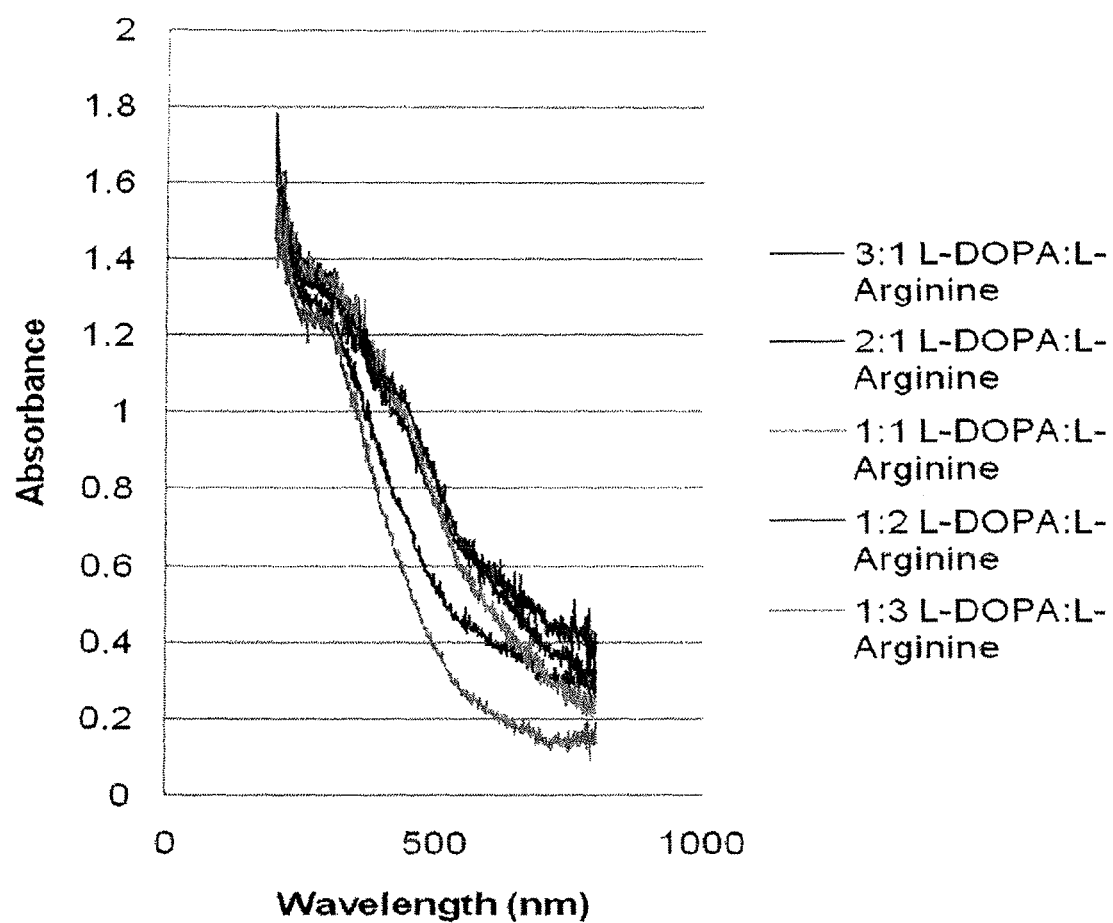
Figure 21:
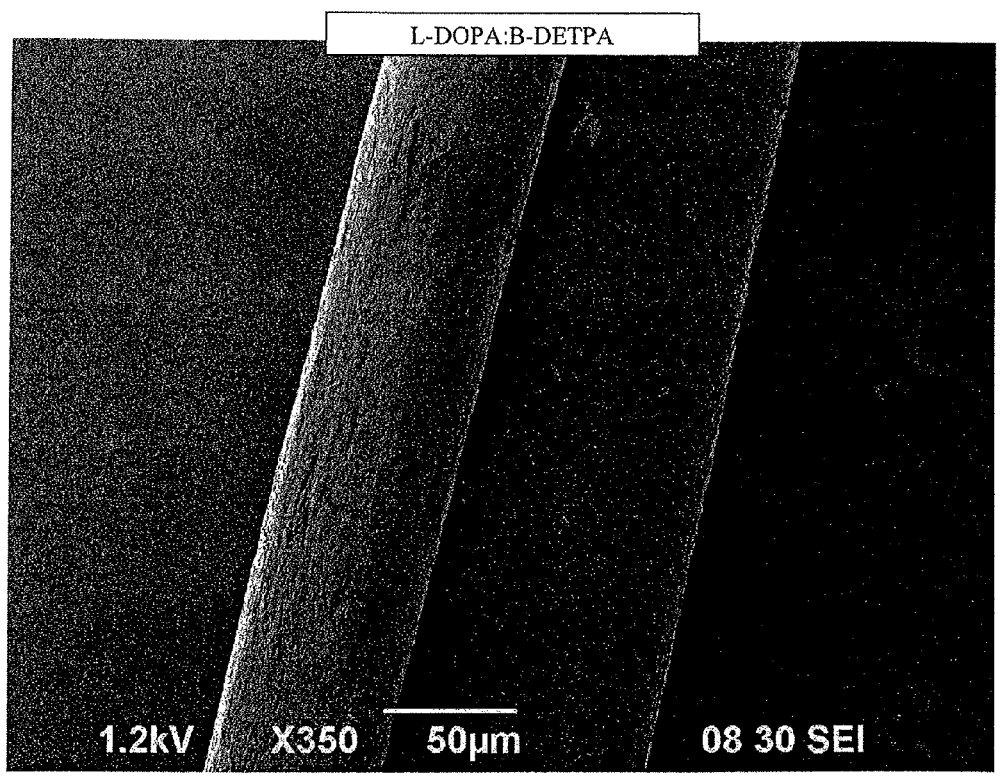
Figure 22:
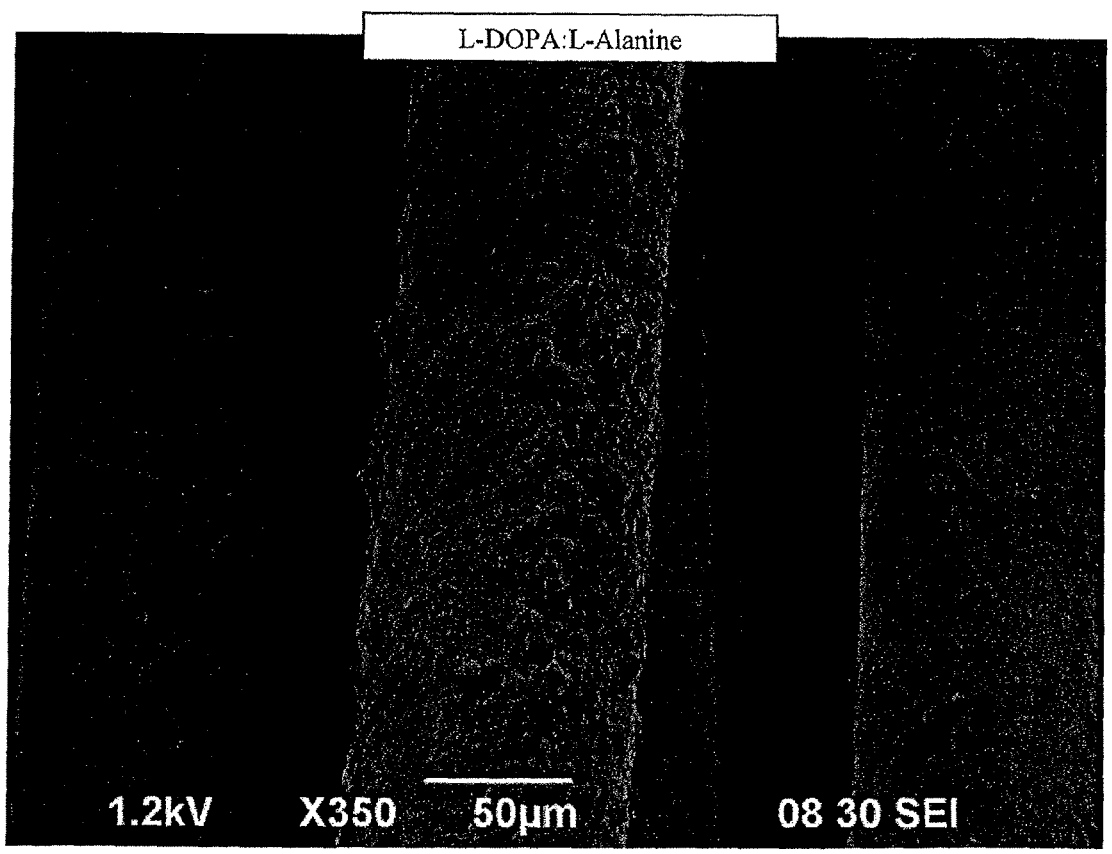
Figure 23:
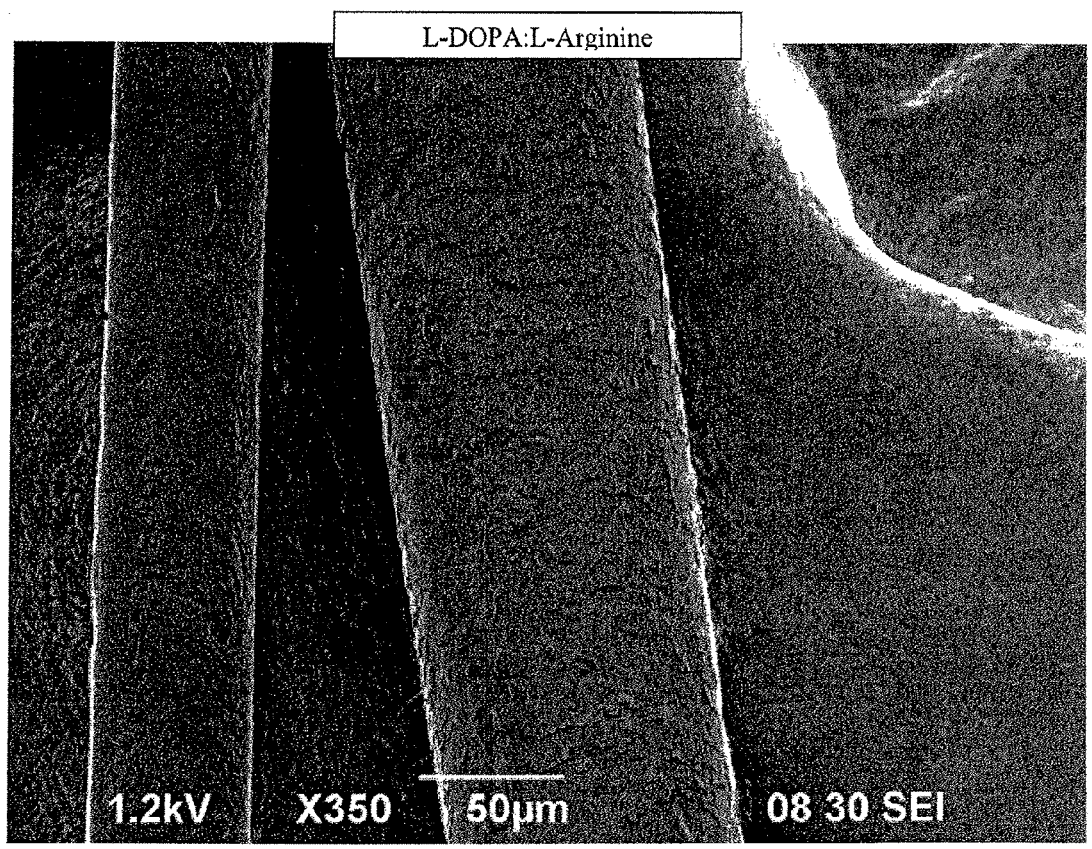
Figure 24:
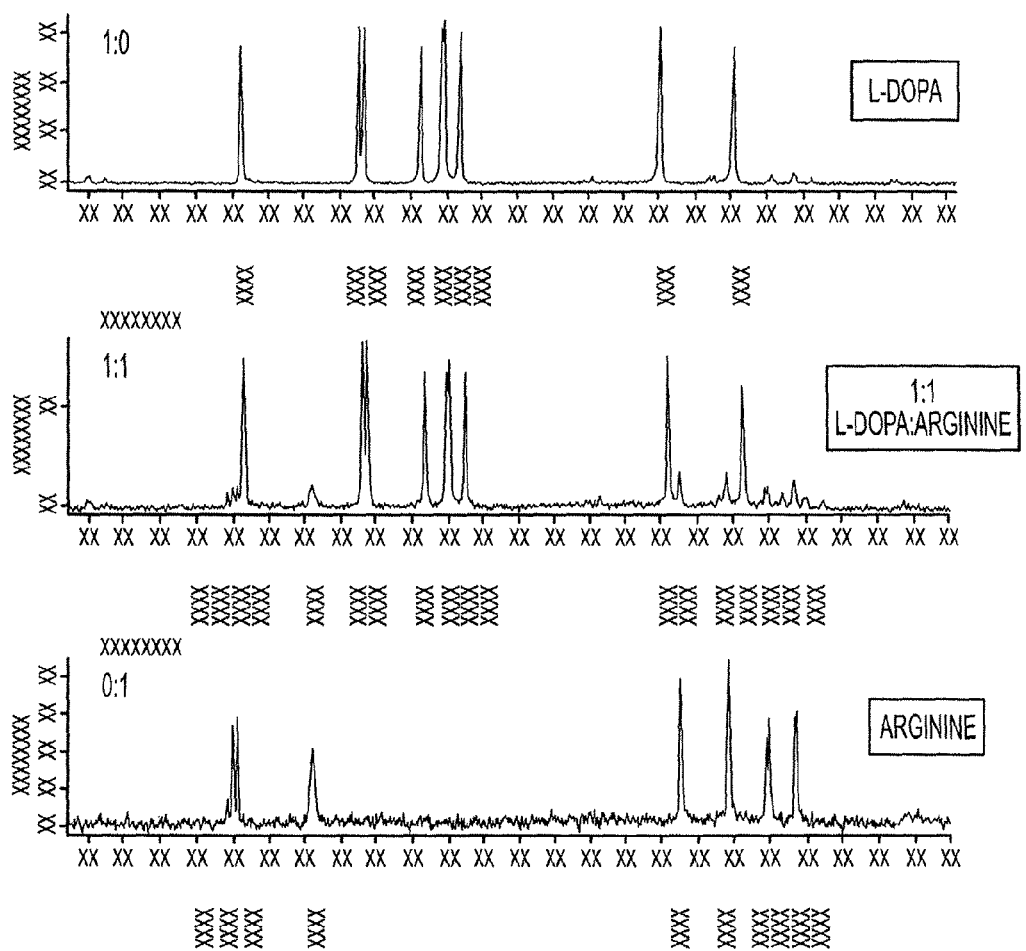
Figure 25A:
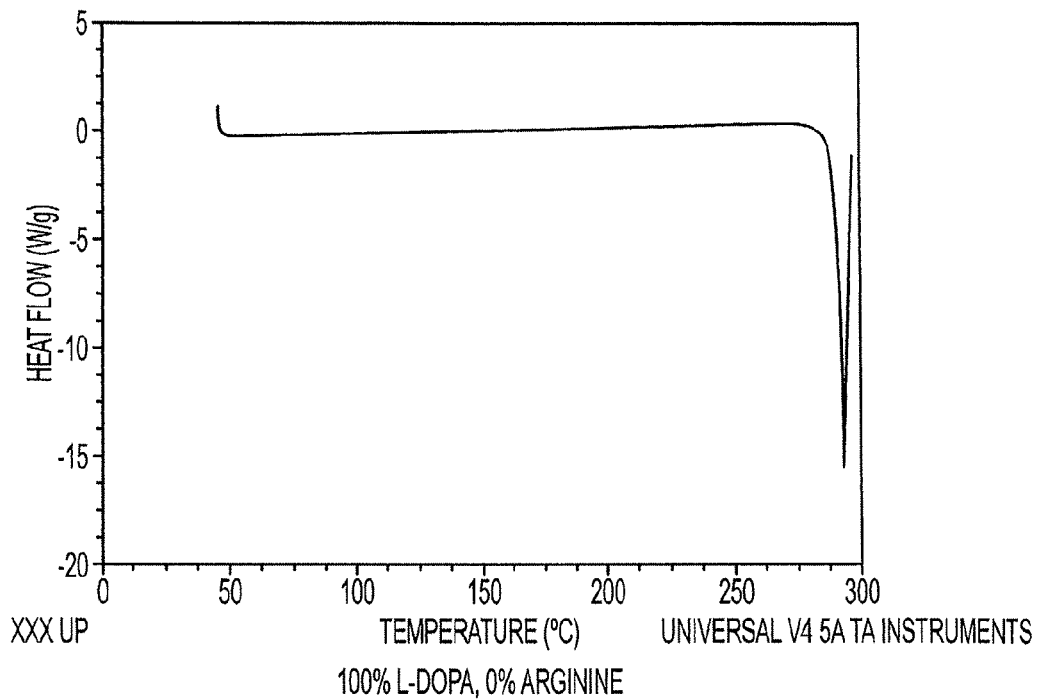
Figure 25B:
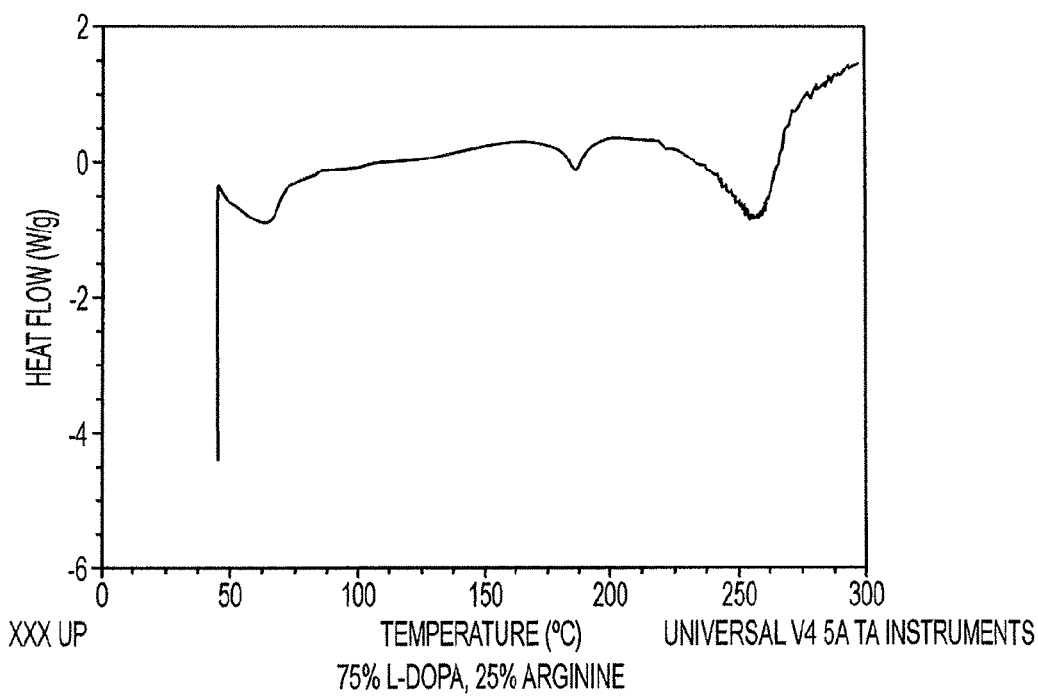
Figure 25C:
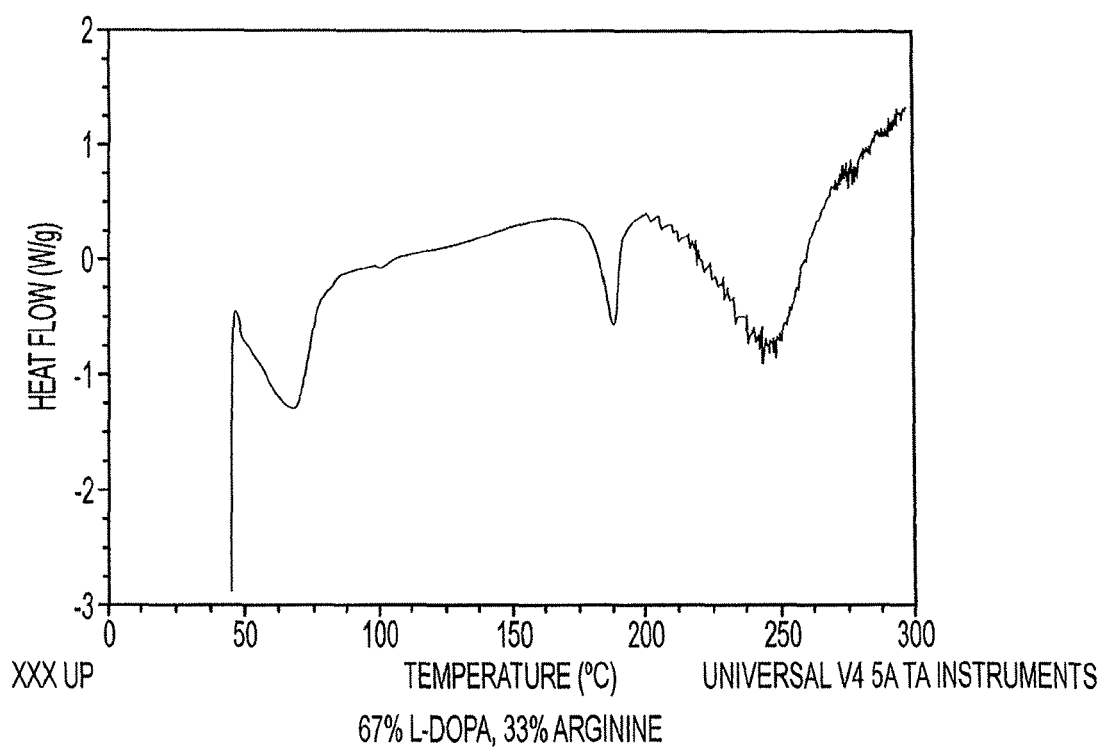
Figure 25D:
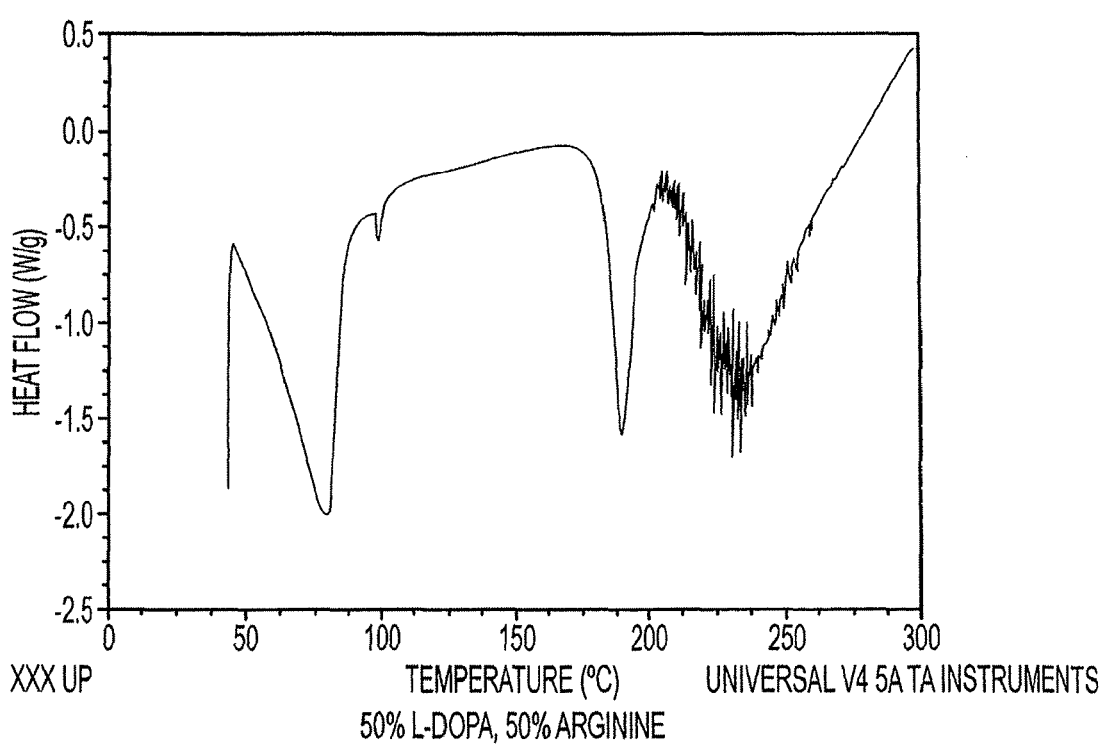
Figure 25E:
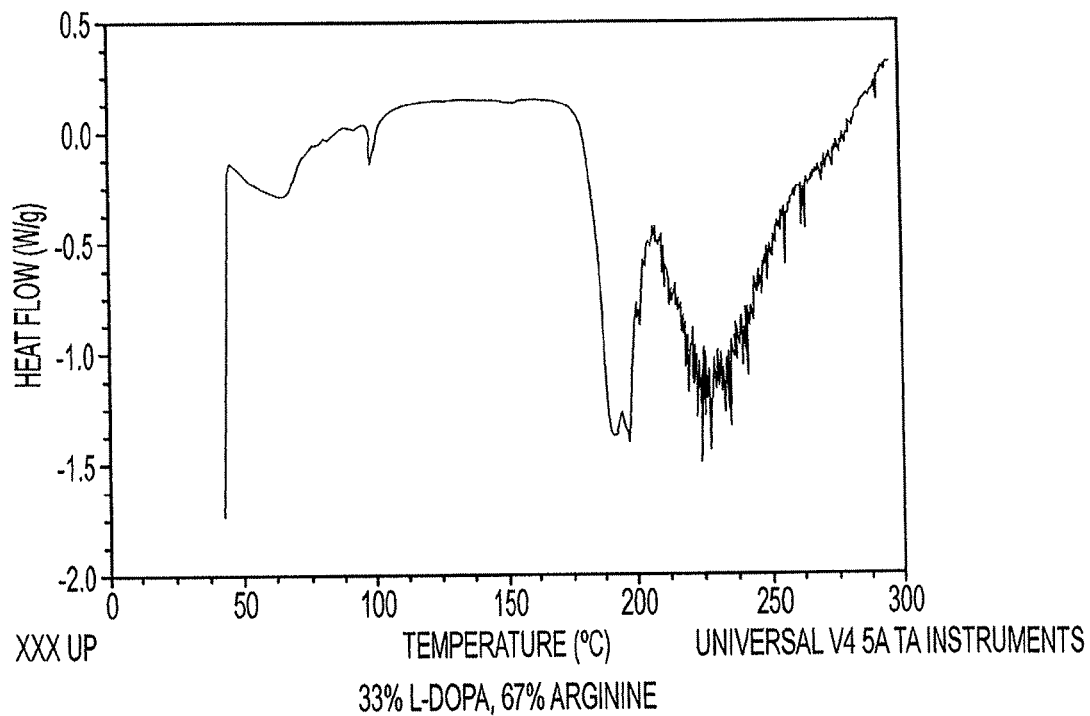
Figure 25F:
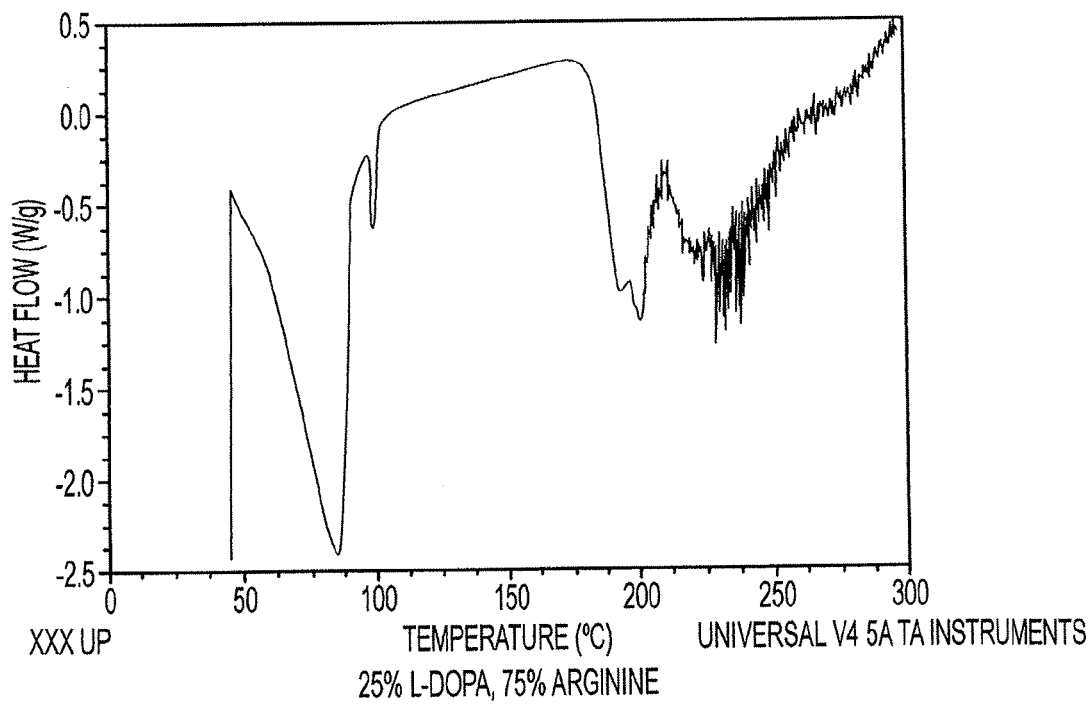
Figure 25G:
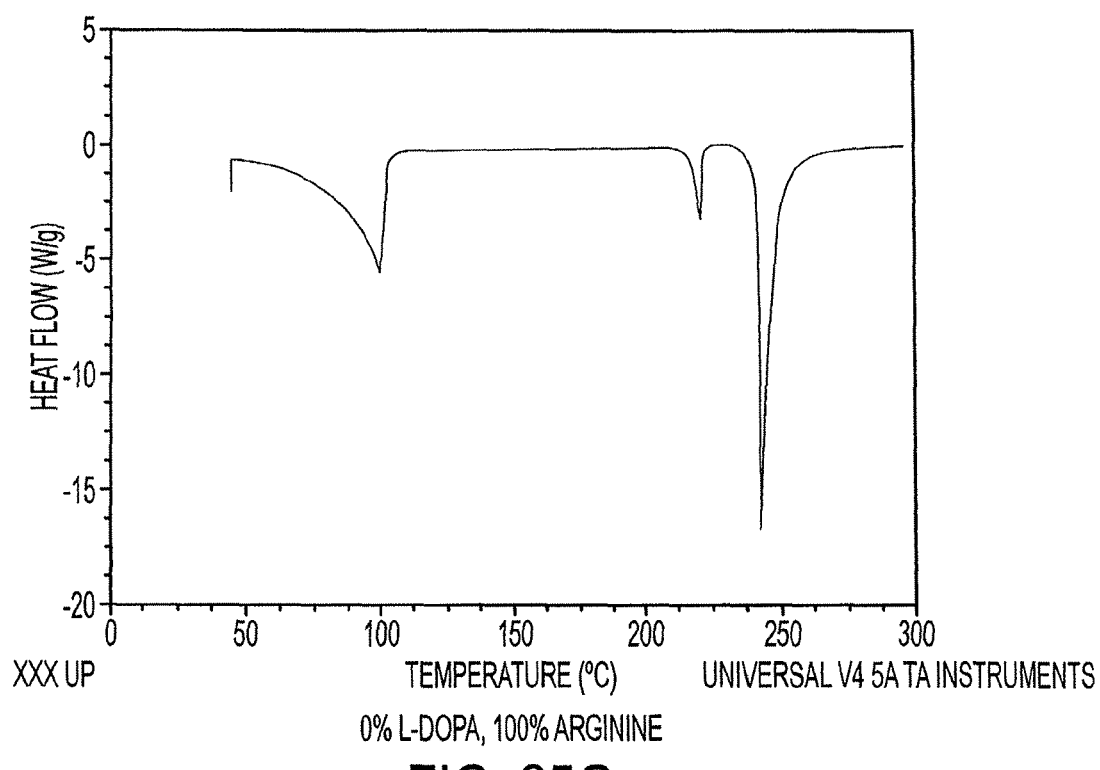

FIGS. 4A, 4B, and 4C are graphs of UV-Vis results using colored or control hair samples following L-DOPA treatments according to one embodiment of the present invention;

FIGS. 5A, 5B, and 5C are scanning electron microscopy ("SEM") images of colored or control hair samples following L-DOPA treatments according to one embodiment of the present invention;

FIGS. 6A and 6B are graphs of UV-Vis results using colored or control hair samples following L-DOPA treatments according to one embodiment of the present invention;

FIGS. 7A-7D are scanning electron microscopy ("SEM") images of colored or control hair samples following L-DOPA treatments according to one embodiment of the present invention;

FIG. 8 is a graph of UV-Vis results using colored or control hair samples following L-DOPA treatments according to one embodiment of the present invention;

FIG. 9 is scanning electron microscopy ("SEM") images of colored or control hair samples following L-DOPA treatments according to one embodiment of the present invention;

FIG. 10 is a graph of UV-Vis results using colored or control hair samples following L-DOPA treatments according to one embodiment of the present invention;

FIG. 11 is a graph of UV-Vis results using colored or control hair samples following L-DOPA treatments according to one embodiment of the present invention;

FIG. 12 is a graph of UV-Vis results using colored or control hair samples following L-DOPA treatments according to one embodiment of the present invention;

FIG. 13 is a graph of UV-Vis results using colored or control hair samples following L-DOPA treatments according to one embodiment of the present invention;

FIG. 14 is a graph of UV-Vis results using colored or control hair samples following L-DOPA treatments according to one embodiment of the present invention;

FIG. 15 is a graph of UV-Vis results using colored or control hair samples following L-DOPA treatments according to one embodiment of the present invention;

FIG. 16 is a graph of UV-Vis results using colored or control hair samples following L-DOPA treatments according to one embodiment of the present invention;

FIG. 17 is a graph of UV-Vis results using hair samples following treatment with varying ratios of L-DOPA:B-DETPA according to one embodiment of the present invention;

FIG. 18 is a graph of UV-Vis results using hair samples following treatment with varying ratios of L-DOPA:L-Cysteine according to one embodiment of the present invention;

FIG. 19 is a graph of UV-Vis results using hair samples following treatment with varying ratios of L-DOPA:L-Alanine according to one embodiment of the present invention;

FIG. 20 is a graph of UV-Vis results using hair samples following treatment with varying ratios of L-DOPA:L-Arginine according to one embodiment of the present invention;

FIG. 21 is SEM images of hair samples following treatment with L-DOPA:B-DETPA according to one embodiment of the present invention FIG. 22 is SEM images of hair samples following treatment with L-DOPA:L-Alanine according to one embodiment of the present invention;

FIG. 23 is SEM images of hair samples following treatment with L-DOPA:L-Arginine according to one embodiment of the present invention;

FIG. 24 is a graph of nuclear magnetic resonance of L-DOPA, 1:1 L-DOPA:L-Arginine, and L-Arginine;

FIG. 25A is a graph of differential scanning calorimetry ("DSC") results using 100% L-DOPA, 0% Arginine according to one embodiment of the present invention;

FIG. 25B is a graph of DSC results using approximately 75% L-DOPA, 25% Arginine according to one embodiment of the present invention;

FIG. 25C is a graph of DSC results using approximately 67% L-DOPA, 33% Arginine according to one embodiment of the present invention;

FIG. 25D is a graph of DSC results using approximately 50% L-DOPA, 50% Arginine according to one embodiment of the present invention;

FIG. 25E is a graph of DSC results using approximately 33% L-DOPA, 67% Arginine according to one embodiment of the present invention;

FIG. 25F is a graph of DSC results using approximately 25% L-DOPA, 75% Arginine according to one embodiment of the present invention; and FIG. 25G is a graph of DSC results using approximately 0% L-DOPA, 100% Arginine according to one embodiment of the present invention.

DETAILED DESCRIPTION OF THE INVENTION

Figure 1:
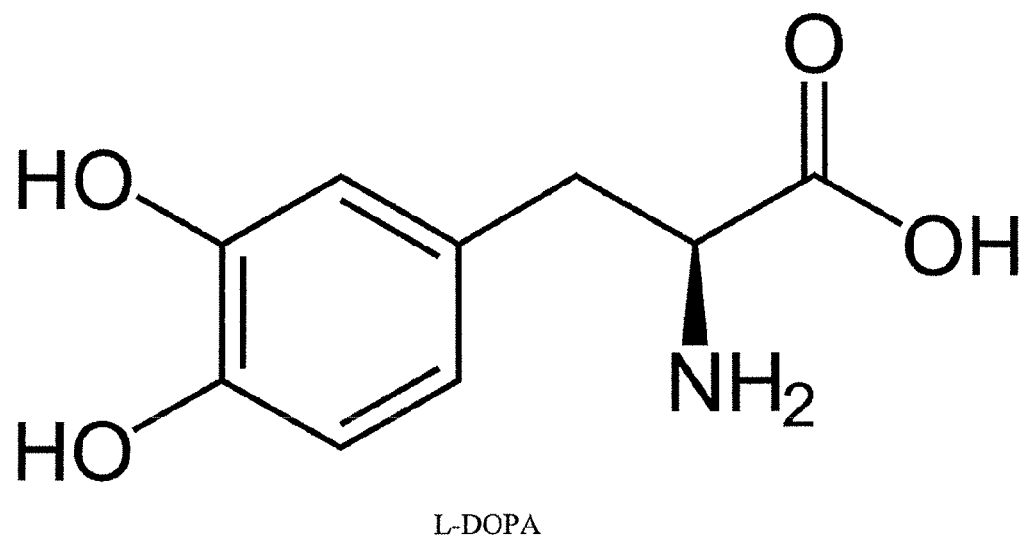
FIG. 1 is the molecular structure of L-3,4-dihydroxyphenylalanine ("L-DOPA") according to one embodiment of the present invention.

Described herein is a new organic coloring composition for coloring materials, and a method of its use. The coloring composition includes natural precursor aromatic ring molecules that form conjugated color polymers upon oxidation. According to one embodiment, the natural precursor aromatic ring molecule is the amino acid L-3,4-dihydroxyphenylalanine ("L-DOPA"), also known by the INN "levodopa" or the IUPAC name (S)-2-amino-3-(3,4-dihydroxyphenyl) propanoic acid, the molecular structure of which is depicted in FIG. 1. In one embodiment, extracts from seeds containing L-DOPA are used in the coloring composition.

The L-DOPA molecules are oxidatively oligomerized or polymerized in the presence of an activator to form colored compounds that dye a material. The activator can be any compound, molecule, or chemical that oxidizes or induces oxidation of the aromatic ring precursor molecules, and can be present in stoichiometric or sub-stoichiometric quantities. In one embodiment, the activator is a salt or an enzyme, including tyrosinase, potassium hexacyanoferrate ("PFH") potassium bicarbonate, and combinations thereof. Extracts from mushrooms containing tyrosinase have been shown to be effective. The coloring composition can also include a buffer such as a phosphate buffer.

Also described herein are methods of use or application of the novel coloring compositions. One embodiment of a method of application comprises the step of combining two aqueous solutions or suspensions, one solution or suspension comprising a color precursor and the other solution or suspension comprising an activator. When combined these reagents form a coloring composition suitable to color a material.

The procedures and examples described below may be employed for the preparation and use of the novel coloring compositions according to one or more embodiments of the present invention. The starting materials and reagents used in preparing these compounds are either available from commercial suppliers such as the Aldrich Chemical Company (Milwaukee, Wis.), Bachem (Torrance, Calif.), Sigma (St. Louis, Mo.), or Worthington Biochemical Corp. (Lakewood, N.J.), or are prepared by methods well known to a person of ordinary skill in the art, following procedures described in such references as *Fieser and Fieser's Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; *Organic Reactions*, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989, among others. The entire disclosures of all documents cited throughout this application are incorporated herein by reference.

While a number of exemplary embodiments, aspects and variations have been provided herein, those of skill in the art will recognize certain modifications, permutations, additions and combinations and certain sub-combinations of the embodiments, aspects and variations. It is intended that the claims are interpreted to include all such modifications, permutations, additions and combinations and certain sub-combinations of the embodiments, aspects and variations are within their scope.

EXAMPLE 1

Coloring Composition Using a Potassium Hexacyanoferrate and Potassium Bicarbonate Initiator Solution For these experiments, 0.1 g of L-DOPA (purchased from Sigma Aldrich) was added to a watch glass containing a hair sample. To this was added 1 mL of water added and the mixture was combined to form a white suspension. One mL of the initiator solution (4.4 g of potassium hexacyanoferrate and 0.8 g of potassium bicarbonate in 10 mL of water) was added and the sample was left at room temperature for a variable amount of time. The sample was then removed from the solution, allowed to air dry, and subsequently rinsed with water.

Figure 2:
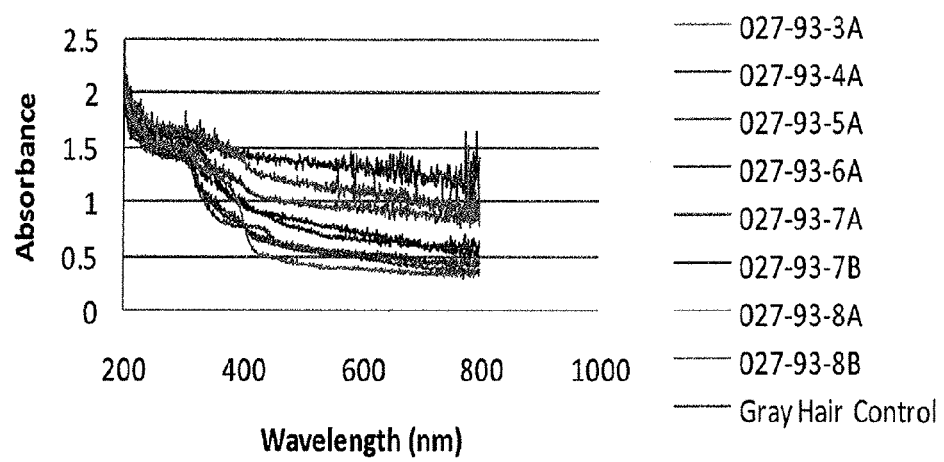
FIG. 2 is a graph of ultraviolet-visible spectroscopy ("UV-Vis") results using colored or control hair samples following L-DOPA treatments according to one embodiment of the present invention.
Figure 3A:
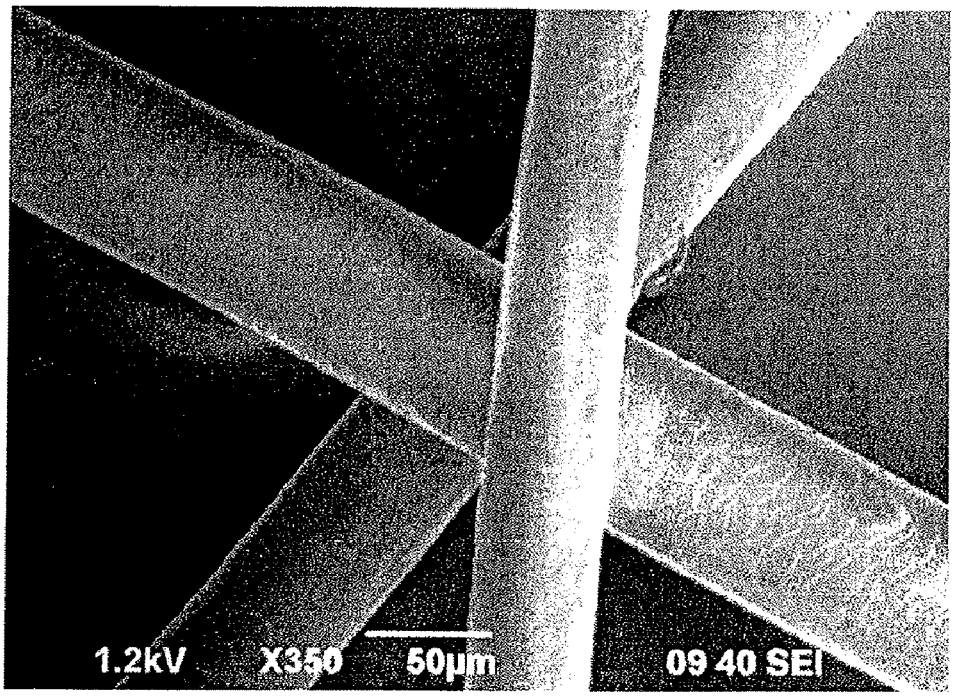
FIGS. 3A and 3B are scanning electron microscopy ("SEM") images of colored or control hair samples following L-DOPA treatments according to one embodiment of the present invention.
Figure 3B:
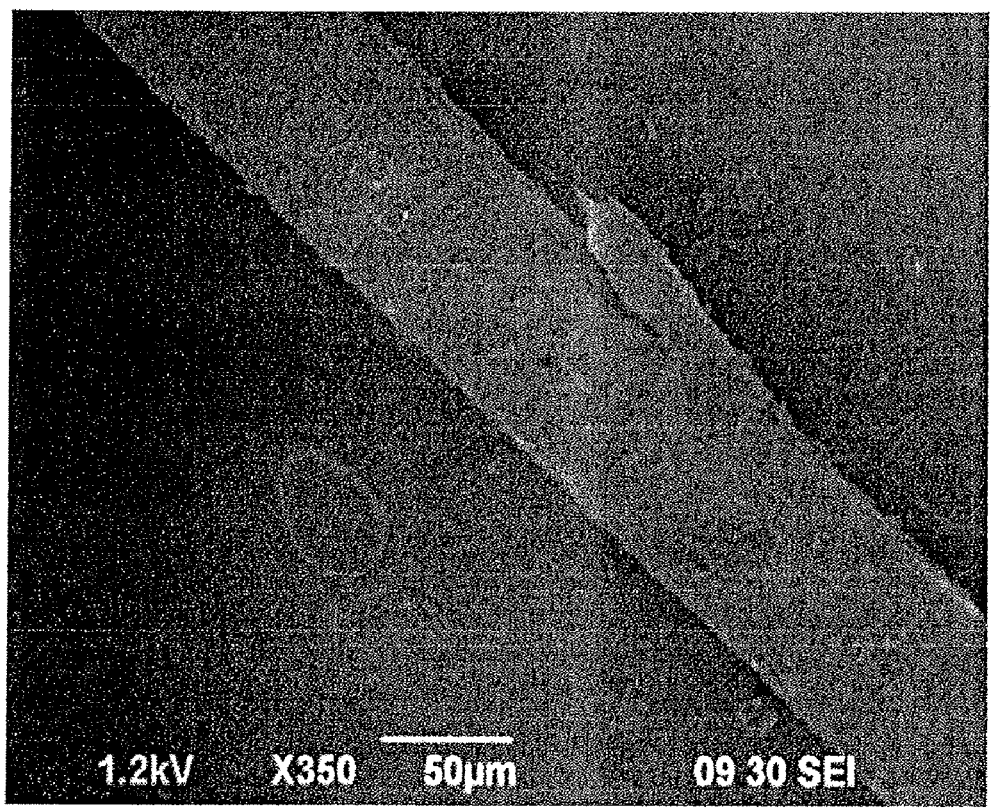

The L-DOPA was oxidized in the presence of the hair shaft, resulting in the formation of a pigment. This dark pigment was polymerized in a coating around the hair shaft, as shown in FIGS. 3A (gray hair control) and 3B (L-DOPA treatment "027-93-7B"), providing structural stability, dark color and reasonable hair texture. Shown in FIG. 2 is a graph of ultraviolet-visible spectroscopy ("UV-Vis") of colored or control hair samples following the hair sample treatments described in TABLE 1.

TABLE 1

Variable Hair Treatment Methods

| Sample # | Hair Treatment |
|---|---|
| Gray Hair Control | NONE |
| 027-93-3A | PHF |
| 027-93-4A | PHF and Potassium Hydrogen Carbonate |
| 027-93-5A | PHF, Potassium Hydrogen Carbonate and L-DOPA |
| 027-93-6A | PHF, Potassium Hydrogen Carbonate and 5,6-dihydroxy indole |
| 037-93-7A | L-DOPA in water |
| 037-93-7B | L-DOPA soak followed by treatment with PHF and Potassium Hydrogen Carbonate |
| 027-93-8A | L-DOPA and Potassium Hydrogen Carbonate |
| 027-93-8B | L-DOPA and base soak followed by treatment with PHF and Potassium Hydrogen Carbonate |

EXAMPLE 2

Coloring Compositions with a Potassium Hexacyanoferrate and Potassium Bicarbonate Initiator Solution and Variable Concentrations of L-DOPA It was necessary to determine an optimal concentration of precursor molecule for an optimal coloring composition. For these experiments, the specified amount of L-DOPA was added to a watch glass containing a hair sample. To this was added 1 mL of water added and the mixture was combined to form a white suspension. One mL of the initiator solution (4.4 g of potassium hexacyanoferrate and 0.8 g of potassium bicarbonate in 10 mL of water) was added and the sample was left at room temperature for a variable amount of time. The sample was then removed from the solution, allowed to air dry, and subsequently rinsed with water. TABLE 2 describes the two variables for these experiments: (i) the dyeing time; and (ii) the concentration of L-DOPA.

TABLE 2

Variable Hair Treatment Methods

| Time (mins) | Concentration of L-DOPA (in 1 mL water) | | |
|---|---|---|---|
| | 0.05 g L-DOPA | 0.1 g L-DOPA | 0.25 g L-DOPA |
| 10 | 027-99-1A | 027-97-1A | 027-97-2A |
| 20 | NA | 027-97-1B | 027-97-2B |
| 30 | 027-99-1B | 027-97-1C | 027-97-2C |
| 60 | 027-99-1C | 027-97-1D | 027-97-2D |
| 120 | 027-99-1D | 027-97-1E | 027-97-2E |
| 180 | NA | 027-97-1F | 027-97-2F |
| 240 | 027-99-1E | 027-97-1G | 027-97-2G |
| 300 | NA | 027-97-1H | 027-97-2H |
| 360 | 027-99-1F | NA | NA |
| 480 | 027-99-1G | NA | NA |
| 1440 | 027-99-1H | NA | NA |

The L-DOPA that was oxidized in the varying concentrations showed increasing darkness of pigment at shorter times with increasing L-DOPA concentration. The dark pigments were polymerized in coatings around the hair shaft providing structural stability, dark color and reasonable hair texture. Shown in FIGS. 4A-4C are graphs of UV-Vis results of colored or control hair samples following the hair sample treatments described in TABLE 2. Shown in FIGS. 5A-5C are scanning electron microscopy ("SEM") figures of representative hair samples.

EXAMPLE 3

Coloring Compositions Using an Enzyme Initiator and Variable Dyeing Times

It was hypothesized that polymerization of the precursor molecule could be initiated by an enzyme. In these experiments several different enzymes were used, including tyrosinase and horseradish peroxidase ("HRP"). However, one skilled in the art would recognize that there are many other enzymes which can serve as an initiator in the coloring composition under the desired conditions.

Tyrosinase was examined as an initiator for the coloring composition. Tyrosinase is a copper-containing enzyme found in both plants and humans which, among other functions, catalyzes the production of melanin from tyrosine by oxidation. For these experiments, 0.05 g of L-DOPA was added to a watch glass containing a hair sample. To this was added 1 mL of water added and the mixture was combined to form a white suspension. One mL of the initiator solution (0.004 g USB Tyrosinase and 10 mL aqueous phosphate buffer (pH 7)) was added and the sample was left at room temperature for a variable amount of time. The sample was then removed from the solution, allowed to air dry, and subsequently rinsed with water.

HRP was also examined as an initiator for the coloring composition. HRP is an enzyme that, like tyrosinase, catalyzes the oxidation of its substrate. For these experiments, 0.05 g of L-DOPA was added to a watch glass containing a hair sample. To this was added 1 mL of water added and the mixture was combined to form a white suspension. One mL of the initiator solution (0.008 g Horseradish Peroxidase and 10 mL phosphase buffer) was added and the sample was left at room temperature for a variable amount of time. The sample was then removed from the solution, allowed to air dry, and subsequently rinsed with water.

TABLE 3 describes the length of the dyeing time for both the tyrosinase and the HRP experiments.

TABLE 3

Variable Hair Treatment Methods

| Time (mins) | Initiator | |
|---|---|---|
| | HRP | Tyrosinase |
| 10 | 027-99-2A | 027-99-3A |
| 20 | 027-99-2B | 027-99-3B |
| 30 | 027-99-2C | 027-99-3C |
| 60 | 027-99-2D | 027-99-3D |
| 120 | 027-99-2E | 027-99-3E |
| 180 | 027-99-2F | 027-99-3F |
| 240 | 027-99-2G | 027-99-3G |
| 1440 | 027-99-2H | 027-99-3H |

The L-DOPA was oxidized to some degree in the presence of either HRP or tyrosinase. However, the oxidation was particularly effective using tyrosinase in up to twenty-four hours. FIGS. 6A and 6B are graphs of UV-Vis results of colored or control hair samples following the hair sample treatments described in TABLE 3. Shown in FIGS. 7A-7D are SEM images of representative hair samples.

EXAMPLE 4

Coloring Compositions Using an Enzyme Initiator and Multiple Rounds of Dyeing

For these experiments, 0.05 g of L-DOPA was added to a watch glass containing a hair sample. To this was added 1 mL of water added and the mixture was combined to form a white suspension. One mL of the initiator solution (0.004 g USB Tyrosinase and 10 mL aqueous phosphate buffer (pH 7)) was added and the sample was left at room temperature for a variable amount of time. The sample was then removed from the solution, allowed to air dry, and subsequently rinsed with water. Several of the samples were then subjected to one or more additional rounds of dyeing, as shown in TABLE 4.

TABLE 4

Sample Matrix

| Number of Repeat Dyes (10 mins each) | PHF | Tyrosinase |
|---|---|---|
| 1 | 027-104-1A | 027-104-2A |
| 2 | 027-104-1B | 027-104-2B |
| 3 | 027-104-2C | 027-104-2C |

The oxidized L-DOPA coatings were repeated over three trials. The intensity of the color increased with increasing number of dyes. The increase in color was particularly effective using tyrosinase initiator. FIG. 8 is a graph of UV-Vis results of colored or control hair samples following the hair sample treatments described in TABLE 4. Shown in FIG. 9 are SEM images of representative hair samples.

EXAMPLE 5

Coloring Compositions Using Enzyme Initiators with Different Enzymatic Activity

It was hypothesized that using enzymes with varying activities might vary the effects of the coloring composition or its use. For these experiments, 0.05 g of L-DOPA was added to a watch glass containing a hair sample. To this was added 1 mL of water added and the mixture was combined to form a white suspension. One mL of the initiator solution (0.004 g enzyme and 10 mL aqueous phosphate buffer (pH 7)) was added and the sample was left at room temperature for a variable amount of time. The sample was then removed from the solution, allowed to air dry, and subsequently rinsed with water. The variables of the experiments are depicted in TABLE 5. Enzymes with varying activity were obtained from the following: (i) tyrosinase from the Worthington Biochemical Corp. with ≧500 units per mg; and (ii) tyrosinase from USB Corporation (Cleveland, Ohio) with 1590 units per mg.

TABLE 5

Sample Matrix

| Worthington Tyrosinase (550 units/mg) | | | USB Tyrosinase (1590 units/mg) | | |
|---|---|---|---|---|---|
| Sample # | L-DOPA (g) | Time (min) | Sample # | L-DOPA (g) | Time (min) |
| 041-2-1 | 0.0498 | 10 | 041-4-1 | 0.0513 | 10 |
| 041-2-2 | 0.05 | 20 | 041-4-2 | 0.049 | 20 |
| 041-2-3 | 0.0502 | 30 | 041-4-3 | 0.0498 | 30 |
| 041-2-4 | 0.0506 | 60 | 041-4-4 | 0.0502 | 60 |
| 041-2-5 | 0.0509 | 120 | 041-4-5 | 0.0505 | 120 |
| 041-2-6 | 0.0506 | 180 | 041-4-6 | 0.051 | 180 |
| 041-2-7 | 0.0508 | 240 | 041-4-7 | 0.0518 | 240 |
| 041-2-8 | 0.0509 | 1440 | 041-4-8 | 0.0499 | 1440 |

For both the Worthington tyrosinase and the USB tyrosinase, 0.004 g of the tyrosinase was suspended in 10 mL of phosphate buffer. As shown in FIG. 10, the L-DOPA oxidized to a more intense pigment color in a shorter period using tyrosinase with a higher activity level (i.e., the USB tyrosinase in these experiments).

EXAMPLE 6

Coloring Compositions at Increased Temperatures Using Enzyme Initiators with Different Enzymatic Activity It was then hypothesized that the coloring composition might be more effective at higher temperatures. For these experiments, 0.05 g of L-DOPA was added to a watch glass containing a hair sample. To this was added 1 mL of water added and the mixture was combined to form a white suspension. One mL of the initiator solution (0.004 g enzyme and 10 mL aqueous phosphate buffer (pH 7)) was added and the sample was left at 35° C. or 45° C. for an allotted time. The sample was then removed from the solution, allowed to air dry, and subsequently rinsed with water. The variables of the experiments are depicted in TABLE 6.

TABLE 6

Sample Matrix

| Worthington Tyrosinase | | | | USB Tyrosinase | | | |
|---|---|---|---|---|---|---|---|
| 35° C. | | 45° C. | | 35° C. | | 45° C. | |
| Sample # | Time (min) | Sample # | Time (min) | Sample # | Time (min) | Sample # | Time (min) |
| 041-3-1 | 10 | 041-5-1 | 10 | 041-L-1 | 10 | 041-6-1 | 10 |
| 041-3-2 | 20 | 041-5-2 | 20 | 041-L-2 | 20 | 041-6-2 | 20 |
| 041-3-3 | 30 | 041-5-3 | 30 | 041-L-3 | 30 | 041-6-3 | 30 |
| 041-3-4 | 40 | 041-5-4 | 40 | 041-L-4 | 40 | 041-6-4 | 40 |
| 041-3-5 | 50 | 041-5-5 | 50 | 041-L-5 | 50 | 041-6-5 | 50 |
| 041-3-6 | 60 | 041-5-6 | 60 | 041-L-6 | 60 | 041-6-6 | 60 |
| 041-3-7 | 120 | 041-5-7 | 120 | 041-L-7 | 120 | 041-6-7 | 120 |
| 041-3-8 | 180 | 041-5-8 | 180 | 041-L-8 | 180 | 041-6-8 | 180 |

For both the Worthington tyrosinase and the USB tyrosinase, 0.004 g of the tyrosinase was suspended in 10 mL of phosphate buffer. As shown in FIG. 11, both the rate and efficacy of tyrosinase-catalyzed L-DOPA oxidation increased.

EXAMPLE 7

Coloring Compositions at Increased Temperatures Using Enzyme Initiators with Different Enzymatic Activity and a Water Buffer It was next hypothesized that varying the buffer might vary the activity of the coloring composition and thus vary the outcome of the dyeing procedure. For these experiments, 0.05 g of L-DOPA was added to a watch glass containing a hair sample. To this was added 1 mL of water added and the mixture was combined to form a white suspension. One mL of the initiator solution (0.004 g enzyme and 10 mL water)) was added and the sample was left at room temperature, 35° C., or 45° C. for an allotted time. The sample was then removed from the solution, allowed to air dry, and subsequently rinsed with water. The variables of the experiments are depicted in TABLE 7.

TABLE 7

Sample Matrix

| Worthington Tyrosinase | | | | USB Tyrosinase | | | | | |
|---|---|---|---|---|---|---|---|---|---|
| RT | | 35° C. | | RT | | 35° C. | | 45° C. | |
| Sample # | Time (min) | Sample # | Time (min) | Sample # | Time (min) | Sample # | Time (min) | Sample # | Time (min) |
| 041-H-1 | 10 | 041-J-1 | 10 | 041-I-1 | 10 | 041-K-1 | 10 | 041-G-1 | 10 |
| 041-H-2 | 20 | 041-J-2 | 20 | 041-I-2 | 20 | 041-K-2 | 20 | 041-G-2 | 20 |
| 041-H-3 | 30 | 041-J-3 | 30 | 041-I-3 | 30 | 041-K-3 | 30 | 041-G-3 | 30 |
| 041-H-4 | 40 | 041-J-4 | 40 | 041-I-4 | 40 | 041-K-4 | 40 | 041-G-4 | 40 |
| 041-H-5 | 50 | 041-J-5 | 50 | 041-I-5 | 50 | 041-K-5 | 50 | 041-G-5 | 50 |
| 041-H-6 | 60 | 041-J-6 | 60 | 041-I-6 | 60 | 041-K-6 | 60 | 041-G-6 | 60 |

TABLE 7-continued

| Sample Matrix | | | | | | | | | |
|---|---|---|---|---|---|---|---|---|---|
| Worthington Tyrosinase | | | | USB Tyrosinase | | | | | |
| RT | | 35° C. | | RT | | 35° C. | | 45° C. | |
| Sample # | Time (min) | Sample # | Time (min) | Sample # | Time (min) | Sample # | Time (min) | Sample # | Time (min) |
| 041-H-7 | 120 | 041-J-7 | 120 | 041-I-7 | 120 | 041-K-7 | 120 | 041-G-7 | 120 |
| 041-H-8 | 180 | 041-J-8 | 180 | 041-I-8 | 180 | 041-K-8 | 180 | 041-G-8 | 180 |

For both the Worthington tyrosinase and the USB tyrosinase, 0.004 g of the tyrosinase was suspended in 10 mL of phosphate buffer. As shown in FIG. 12, at both room temperature and the increased temperatures the rate and efficacy of the tyrosinase-catalyzed L-DOPA oxidation was dramatically increased by the use of a water solution in place of the phosphate buffer.

EXAMPLE 8

Optimizing Shade Range by Adjusting Enzyme Concentration

To examine the effect of reduced concentration of enzyme, the following experiments were performed with $1/10^{th}$ the concentration of the enzyme, with the samples as depicted in TABLE 8.

TABLE 8

| Sample Matrix | | | | | |
|---|---|---|---|---|---|
| RT | | 45° C. | | 55° C. | |
| Sample # | Time (min) | Sample # | Time (min) | Sample # | Time (min) |
| 041-A-1 | 10 | 041-C-1 | 10 | 041-E-1 | 10 |
| 041-A-2 | 20 | 041-C-2 | 20 | 041-E-2 | 20 |
| 041-A-3 | 30 | 041-C-3 | 30 | 041-E-3 | 30 |
| 041-A-4 | 40 | 041-C-4 | 40 | 041-E-4 | 40 |
| 041-A-5 | 50 | 041-C-5 | 50 | 041-E-5 | 50 |
| 041-A-6 | 60 | 041-C-6 | 60 | 041-E-6 | 60 |
| 041-A-7 | 120 | 041-C-7 | 120 | 041-E-7 | 120 |
| 041-A-8 | 180 | 041-C-8 | 180 | 041-E-8 | 180 |

As shown in FIG. 13, the reduction of enzyme concentration lowered the rate and efficacy of tyrosinase-catalyzed L-DOPA oxidation.

The coloring composition can further include a coloring agent. In a preferred embodiment, the color agent is an organic compound. Examples of organic compounds that can be used as a colorant include emodin, often isolated from rhubarb or buckthorn, curcumin which is commonly isolated from turmeric, and lawsone which is commonly isolated from the henna plant. Other organic dyes include plumbogen, jugalone, and amino acid combinations. Those skilled in the art will recognize that there are hundreds of organic compounds which are known to serve as dyeing agents. Following are exemplary formulations of the coloring composition including one or more colorants to enhance coloring.

EXAMPLE 9

Using Emodin as a Colorant

In these experiments, the ingredients listed in TABLE 9 were used. Emodin (6-methyl-1,3,8-trihydroxyanthraquinone) was combined with L-DOPA and ground to ensure sufficient homogeneity. The sodium bicarbonate was dissolved in water, and the L-DOPA/emodin mixture was combined with the sodium bicarbonate solution. This formed the coloring composition which was then used to color a material. In one line of experiments, the material was exposed to the composition under heat for up to 24 hours at 55° C., with approximately 1 hour being optimal for most dyeing purposes. The material was air dried and rinsed with room temperature water.

TABLE 9

| Coloring Composition Comprising Emodin | |
|---|---|
| Ingredient | Amount |
| Emodin | 1.059 g |
| L-DOPA | 0.441 g |
| Sodium bicarbonate | 3.12 g |
| Water | 60 ml |

EXAMPLE 10

Using Curcumin and Lawsone as a Colorant

In these experiments, the ingredients listed in TABLE 10 were used. Curcumin ((1E,6E)-1,7-bis(4-hydroxy-3-methoxyphenyl)-1,6-heptadiene-3,5-dione) and lawsone (2-hydroxy-1,4-naphthoquinone) were combined with L-DOPA and ground to ensure sufficient homogeneity. The sodium bicarbonate was dissolved in water, and the L-DOPA/curcumin/lawsone mixture was combined with the sodium bicarbonate solution. This formed the coloring composition which was then used to color a material. In one line of experiments, the material was exposed to the composition under heat for up to 24 hours at 55° C., with approximately 1 hour being optimal for most dyeing purposes. The material was air dried and rinsed with room temperature water.

TABLE 10

| Coloring Composition Comprising Curcumin and Lawsone | |
|---|---|
| Ingredient | Amount |
| Curcumin | 0.147 g |
| L-DOPA | 0.249 g |
| Lawsone | 0.081 g |
| Sodium bicarbonate | 3.12 g |
| Water | 60 ml |

EXAMPLE 11

Using Emodin, Curcumin and Lawsone as a Colorant

In these experiments, the ingredients listed in TABLE 11 were used. Curcumin, lawsone, and emodin were combined with L-DOPA and ground to ensure sufficient homogeneity. The sodium bicarbonate was dissolved in water, and the L-DOPA/curcumin/lawsone/emodin mixture was combined with the sodium bicarbonate solution. This formed the coloring composition which was then used to color a material. In one line of experiments, the material was exposed to the composition under heat for up to 24 hours at 55° C., with approximately 1 hour being optimal for most dyeing purposes. The material was air dried and rinsed with room temperature water.

TABLE 11

| Coloring Composition Comprising Emodin, Curcumin and Lawsone | |
|---|---|
| Ingredient | Amount |
| Curcumin | 0.106 g |
| L-DOPA | 0.0238 g |
| Lawsone | 0.0193 g |
| Emodin | 0.0159 g |
| Sodium bicarbonate | 3.12 g |
| Water | 60 ml |

EXAMPLE 12

Ratio of Curcumin, Lawsone, Jugalone, Plumbagin, and Emodin to L-DOPA

The effects of varying the ratio of organic dye (such as curcumin, lawsone, jugalone, plumbagin, or emodin) to L-DOPA were also analyzed. For these experiments, the material was pre-soaked for 30 min in sodium bicarbonate followed by a 60 min to 24 hr reaction in tyrosinase and the L-DOPA/dye mix. The ratio of organic dye to L-DOPA in one set of experiments is shown in TABLE 12.

TABLE 12

| Ratio of L-DOPA to Organic Dye | | | | | |
|---|---|---|---|---|---|
| curcumin | lawsone | jugalone | plumbagin | emodin | Ratio |
| 041-76-1 | 041-62-1 | 041-78-A | 041-78-1 | 041-75-1 | 1:00 |
| 041-76-2 | 041-62-2 | 041-78-B | 041-78-2 | 041-75-2 | 3:01 |
| 041-76-3 | 041-62-3 | 041-78-C | 041-78-3 | 041-75-3 | 2:01 |
| 041-76-4 | 041-62-4 | 041-78-D | 041-78-4 | 041-75-4 | 1:01 |
| 041-76-5 | 041-62-5 | 041-78-E | 041-78-5 | 041-75-5 | 1:02 |
| 041-76-6 | 041-62-6 | 041-78-F | 041-78-6 | 041-75-6 | 1:03 |
| 041-76-7 | 041-62-7 | 041-78-G | 041-78-7 | 041-75-7 | 0:01 |

The varying ratios resulted in varying shades of color.

EXAMPLE 13

Optimizing Shade Range Using Amino Acid Blends

To further optimize the shade range of the coloring composition, amino acid blends were added to the composition and examined for their ability to color material. For these experiments, the material was exposed to up to a 24 hour reaction in tyrosinase and the L-DOPA/amino acid mix. The ratio of amino acid to L-DOPA in one set of experiments is shown in TABLE 13.

TABLE 13

| Ratio of L-DOPA to Amino Acid | | | | |
|---|---|---|---|---|
| L-cysteine | methionine | cystine | glutamine | Ratio |
| 041-10-1 | 041-11-1 | 041-16-1X | 041-12-1 | 1:00 |
| 041-10-2 | 041-11-2 | 041-16-2X | 041-12-2 | 3:01 |
| 041-10-3 | 041-11-3 | 041-16-3X | 041-12-3 | 2:01 |
| 041-10-4 | 041-11-4 | 041-16-4X | 041-12-4 | 1:01 |
| 041-10-5 | 041-11-5 | 041-16-5X | 041-12-5 | 1:02 |
| 041-10-6 | 041-11-6 | 041-16-6X | 041-12-6 | 1:03 |
| 041-10-7 | 041-11-7 | 041-16-7X | 041-12-7 | 0:01 |

The varying ratios resulted in varying shades of color.

EXAMPLE 14

Reducing pH of the Coloring Composition

To determine the effects of pH on the ability of the coloring composition to color material, a series of experiments were performed in which the pH of one or more of the solutions was altered. In one set of experiments, the water normally used in the solution was replaced with a 0.3125% citric acid solution. Although the citric acid improved the texture of the hair in these experiments, the lowered pH resulted in reduced darkness of color.

EXAMPLE 15

Organic Sources of L-DOPA and Tyrosinase

Since there is a continued need for a completely organic coloring composition, organic sources of L-DOPA and tyrosinase were researched. For example, tyrosinase can be isolated from a variety of natural products, including potato and edible fungi (such as white button mushrooms), avocados, tomatoes, and many others. In the following experiments, a crude tyrosinase extract from white button mushrooms was obtained and examined at several different temperatures for its ability to oxidize L-DOPA, as shown in TABLE 14.

TABLE 14

| Natural Tyrosinase Sample Matrix | | | | | |
|---|---|---|---|---|---|
| RT | | 35° C. | | 45° C. | |
| 041-7-1 | 10 | 041-8-1 | 10 | 041-B-1 | 10 |
| 041-7-2 | 20 | 041-8-2 | 20 | 041-B-2 | 20 |
| 041-7-3 | 30 | 041-8-3 | 30 | 041-B-3 | 30 |
| 041-7-4 | 60 | 041-8-4 | 60 | 041-B-4 | 60 |
| 041-7-5 | 120 | 041-8-5 | 120 | 041-B-5 | 120 |
| 041-7-6 | 180 | 041-8-6 | 180 | 041-B-6 | 180 |
| 041-7-7 | 240 | 041-8-7 | 240 | 041-B-7 | 240 |
| 041-7-8 | 1440 | 041-8-8 | 1440 | 041-B-8 | 1440 |

The organic tyrosinase appeared to function in the coloring composition similar to the tyrosinase obtained from commercial sources. See, for example, FIG. 14.

L-DOPA can also be obtained from natural sources, including from velvet beans. In the following experiments, L-DOPA purified from velvet beans was purchased from a commercial source (Sigma-Aldrich) to examine how it would perform in the coloring composition, as shown in TABLE 15. For the RT experiments, both natural L-DOPA and natural tyrosinase (from white button mushroom extract) were used.

TABLE 15

Natural L-DOPA Sample Matrix

| 35° C. | | 45° C. | | RT | |
|---|---|---|---|---|---|
| 041-D-1 | 10 | 041-F-1 | 10 | 041-9-1 | 10 |
| 041-D-2 | 20 | 041-F-2 | 20 | 041-9-2 | 20 |
| 041-D-3 | 30 | 041-F-3 | 30 | 041-9-3 | 30 |
| 041-D-4 | 40 | 041-F-4 | 40 | 041-9-4 | 40 |
| 041-D-5 | 50 | 041-F-5 | 50 | 041-9-5 | 50 |
| 041-D-6 | 60 | 041-F-6 | 60 | 041-9-6 | 60 |
| 041-D-7 | 120 | 041-F-7 | 120 | 041-9-7 | 120 |
| 041-D-8 | 180 | 041-F-8 | 180 | 041-9-8 | 180 |

The organic L-DOPA appeared to function in the coloring composition similar to the synthetic L-DOPA. See, for example, FIG. 15.

EXAMPLE 16

Material Pretreatment

To examine the effect of pretreatment on the ability of the coloring composition to color material, a series of experiments were performed in which the material was pre-treated with one or more solutions. For example, in one set of experiments the material was pretreated with the following: (i) a 10% pullulan solution; (ii) a 10% pullulan/0.625% citric acid solution; (iii) a 20% N-acetyl-cysteine solution; or (iv) a 20% N-acetyl-cysteine/20% urea solution.

EXAMPLE 17

Testing Blends for Increased Stability

Amino acids were also examined for their ability to stabilize the dye and/or color in the material after the material was exposed to the coloring composition. TABLE 16 describes the ratio of L-DOPA to amino acid for one set of experiments.

TABLE 16

Blends Sample Matrix

| Proline | Tryptophan | Tyrosine | Ratio |
|---|---|---|---|
| 041-10-1 | 041-11-1 | 041-16-1X | 1:00 |
| 041-10-2 | 041-11-2 | 041-16-2X | 3:01 |
| 041-10-3 | 041-11-3 | 041-16-3X | 2:01 |
| 041-10-4 | 041-11-4 | 041-16-4X | 1:01 |
| 041-10-5 | 041-11-5 | 041-16-5X | 1:02 |
| 041-10-6 | 041-11-6 | 041-16-6X | 1:03 |
| 041-10-7 | 041-11-7 | 041-16-7X | 0:01 |

The results of these experiments are shown in FIG. 16.

EXAMPLE 18

L-DOPA and Amino Acid NCDs

Amino acids were then used as non-covalent derivitization agents. For these experiments, 0.01 g of an L-DOPA:amino acid blend was added to a watch glass containing a hair sample. One mL of water then added and the mixture was combined to form a white suspension. One mL of the initiator solution (0.004 g enzyme and 10 mL water) was then added and the sample was left at room temperature for twenty-four hours. The sample was then removed from the solution, allowed to air dry, and subsequently rinsed with water. The variables of the experiment are depicted in TABLE 17.

TABLE 17

L-DOPA:Amino Acid Sample Matrix

| Ratio (L-DOPA:X) | B-DEPTA | L-Cysteine | L-Alanine | L-Arginine |
|---|---|---|---|---|
| 1:00 | 027-106-1 | 027-107-1 | 027-108-1 | 027-109-1 |
| 3:1 | 027-106-2 | 027-107-2 | 027-108-2 | 027-109-2 |
| 2:1 | 027-106-3 | 027-107-3 | 027-108-3 | 027-109-3 |
| 1:1 | 027-106-4 | 027-107-4 | 027-108-4 | 027-109-4 |
| 1:2 | 027-106-5 | 027-107-5 | 027-108-5 | 027-109-5 |
| 1:3 | 027-106-6 | 027-107-6 | 027-108-6 | 027-109-6 |
| 0:1 | 027-106-7 | 027-107-7 | 027-108-7 | 027-109-7 |

As shown in the UV-Vis results in FIGS. 17-20, the addition of amino acid NCDs resulted in differing hair color and textures. The SEM images in FIGS. 21-23 show that the experiments resulted in suitable coating of the hair, with slightly different morphologies and colors in each case. Further, the formulations of L-DOPA with non-covalent derivatives resulted in a composition that was more stable to precipitation and agglomerization.

In particular, the L-DOPA and arginine blends showed increased solubility at 1:2 and 1:3 ratios, resulting in a soft texture and a light brown color when applied to the hair samples. As shown in FIGS. 21-28, nuclear magnetic resonance ("NMR") and differential scanning calorimetry ("DSC") experiments using L-DOPA:arginine formulations resulted in specific noncovalent interactions between the L-DOPA and arginine.

EXAMPLE 19

Thickening Agents

According to one embodiment of the coloring composition, the composition can comprise a thickening agent. A thickening agent can cause one or more of the solutions to have a thicker consistency, thus resulting in increased interaction with the material to be dyed. There are numerous thickening agents known in the art, including sodium alginate, which is commonly extracted from algae and is used as a thickening agent in the food industry. Other thickening agents include $CaCO_3$, potassium borate, guar gums, cellulose gums, alginates, xanthane, sclerotium gums, waxes, oils, and other natural and vegetable-based gums. In a preferred embodiment, the thickening agent is a natural and/or organic compound.

According to another embodiment of the coloring composition, the composition can comprise two or more inactive or otherwise unreactive (i.e., incapable of effectively coloring material without the addition of another component) solutions that are mixed, combined, or otherwise placed in communication either just prior to use or during use. For example, solution #1 can include the precursor molecule suspended in solution while solution #2 includes the initiator solution (such as a salt, enzyme, and/or buffer). In another embodiment, the precursor molecule is a powder, paste, gel, or concentrated liquid to which a specified amount of water or other liquid—such as a buffer—must be added by the user. According to a preferred embodiment, the two or more solutions are combined together by the user either just prior to use or during use.

The coloring compositions disclosed herein can be used to permanently or semi-permanently color a material. To color a material, the coloring composition is applied to the material, allowed to penetrate the material for an allotted amount of time, exposed to room temperature or a temperature higher than room temperature if necessary, and subsequently rinsed off the material. The material can be allowed to dry or can be dried according to the prescribed method. If the coloring composition comprises two solutions that must be pre-mixed, the solutions are combined and applied to the material. One embodiment of a method of application comprises the step of combining two aqueous solutions or suspensions, one solution or suspension comprising a color precursor and the other solution or suspension comprising an activator. When combined these reagents form a coloring composition suitable to color a material.

Although the present invention has been described in connection with a preferred embodiment, it should be understood that modifications, alterations, and additions can be made to the invention without departing from the scope of the invention as defined by the claims.

What is claimed is:

1. A coloring composition comprising:
   L-3,4-dihydroxyphenylalanine ("L-DOPA");
   an initiator; and
   L-arginine, wherein said L-DOPA is oxidized in the presence of said initiator to form a color polymer, and further wherein said L-DOPA and said L-arginine form a non-covalent interaction.

2. The coloring composition of claim 1, wherein said L-DOPA is a first solution, and said initiator and said arginine is a second solution.

3. The coloring composition of claim 1, further comprising an amino acid.

4. The coloring composition of claim 3, wherein said amino acid is selected from the group consisting of L-cysteine, L-alanine, L-argenine, and combinations thereof.

5. The coloring composition of claim 1, wherein said initiator is a salt.

6. The coloring composition of claim 5, wherein said salt is selected from the group consisting of potassium hexacyanoferrate, potassium bicarbonate, and combinations thereof.

7. The coloring composition of claim 1, wherein said initiator is a protein.

8. The coloring composition of claim 7, wherein said enzyme is tyrosinase.

9. The coloring composition of claim 1, further comprising a colorant.

10. The coloring composition of claim 9, wherein said colorant is selected from the group consisting of curcumin, lawsone, emodin, jugalone, plumbagin, L-cysteine, methionine, cystine, glutamine, and combinations thereof.

11. The coloring composition of claim 1, wherein said coloring composition comprises organic compounds.

12. The coloring composition of claim 1, further comprising a buffer.

13. The coloring composition of claim 12, wherein said buffer is a phosphate buffer.

14. The coloring composition of claim 1, further comprising a thickening agent.

15. The coloring composition of claim 1, further comprising a stabilizer.

16. The coloring composition of claim 1, wherein the composition is oxidatively stable.

17. A method for dyeing a material, the method comprising the steps:
    mixing a first solution comprising L-3,4-dihydroxyphenylalanine ("L-DOPA") with a second composition comprising an initiator and arginine, wherein said L-DOPA and said arginine form a non-covalent derivatization complex; and
    contacting said material with the mixture.

18. The method of claim 17, where said material is a keratin material.

19. The method of claim 18, wherein said keratin material is hair.

20. The method of claim 17, further comprising the step of leaving said coloring composition in contact with said material for 1 to 60 minutes.

21. The method of claim 17, further comprising the step of pre-treating said material with a third solution.

22. The method of claim 17, further comprising the steps of:
    optionally rinsing said material; and
    optionally drying said material.

* * * * *